United States Patent
Niven et al.

(10) Patent No.: US 6,565,841 B1
(45) Date of Patent: May 20, 2003

(54) PULMONARY ADMINISTRATION OF GRANULOCYTE COLONY STIMULATING FACTOR

(75) Inventors: Ralph Niven, Camarillo, CA (US); Colin G Pitt, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 08/028,087

(22) Filed: Mar. 8, 1993

Related U.S. Application Data

(63) Continuation-in-part of application No. 07/953,208, filed on Sep. 29, 1992, now Pat. No. 5,284,656, which is a continuation of application No. 07/669,792, filed on Mar. 15, 1991, now abandoned.

(51) Int. Cl.[7] .............................................. G09B 11/00
(52) U.S. Cl. ........................................ 424/85.1; 514/12
(58) Field of Search ............................ 424/85.1; 514/2, 514/12; 530/350

(56) References Cited

U.S. PATENT DOCUMENTS

| | | |
|---|---|---|
| 4,002,531 A | 1/1977 | Royer |
| 4,179,337 A | 12/1979 | Davis et al. |
| 4,609,546 A | 9/1986 | HHiratani |
| 4,810,643 A | 3/1989 | Souza |
| 4,904,584 A | 2/1990 | Shaw |

FOREIGN PATENT DOCUMENTS

| | | |
|---|---|---|
| EP | 0 154 316 | 11/1985 |
| EP | 0 257 956 | 3/1988 |
| EP | 0 335 423 | 10/1989 |
| EP | 0 401 384 | 12/1990 |
| EP | 0401384 | * 12/1990 |
| EP | 0 473 268 | 3/1992 |
| EP | 0 539 167 | 4/1993 |
| WO | WO 92/16192 | 10/1992 |

OTHER PUBLICATIONS

Debs et al. "Lung–Specific Delivery . . . " Journ. Immunology 140: 3482–3488 May 15, 1988.*
Takada et al., J. Pharm. Dyn. 1:281–287 (1987). "Evidence for the pulmonary absorption of fluorescent labelled macromolecular compounds".
Niven et al, Pharmaceutical Research 7:990–994 (1990), Solute Absorption from the Airways of the Isolated Rat Lung. III. Absorption of Several Peptidase–Resistant, Synthetic Polypeptides: Poly–(2–Hydroxyethyl–)Aspartamides.
Byron et al; Protein Delivery by Aerosol, In: Polymeric drugs and drug delivery systems 1991, pp. 128–138, Opportunities for Protein Delivery by Aerosol— "Absorption and Retention of Several Synthetic Polypeptides in the Lung".
Byron et al; J. Bioactive and Combatible Polymers 6:25–35 (1991) "Airway Retentionand Pulmonary Absorption of Poly–a, b–[N(2–hydroxyethyl)–D, L–aspartamide]".
Theodore et al; Am J. Physiol. 229:989–996 (1975) "Transalveolar Transport of Large Polar Solutes (sucrose, inulin, and dextran)".
Huchon et al; J. Nucl. Med. 28, 894–902 (1987) "Respiratory Clearance of Aerosolized Radioactive Solutes of Varying Molecular Weight".
Folkesson et al. Scand. 139: 347–354 (1990) "Permeability of the Respiratory Tract to Different–sized Macromolecules after Intratracheal Instilltion in Young and Adult Rats".

(List continued on next page.)

Primary Examiner—Ponnathapu Achutamurthy
Assistant Examiner—Kathleen Kerr
(74) Attorney, Agent, or Firm—Craig A. Crandall; Ron K. Levy; Steven M. Odre

(57) ABSTRACT

Methods and compositions for pulmonary delivery of chemically modified G-CSF, and pegylated proteins are disclosed.

13 Claims, 10 Drawing Sheets

OTHER PUBLICATIONS

Figure 1:
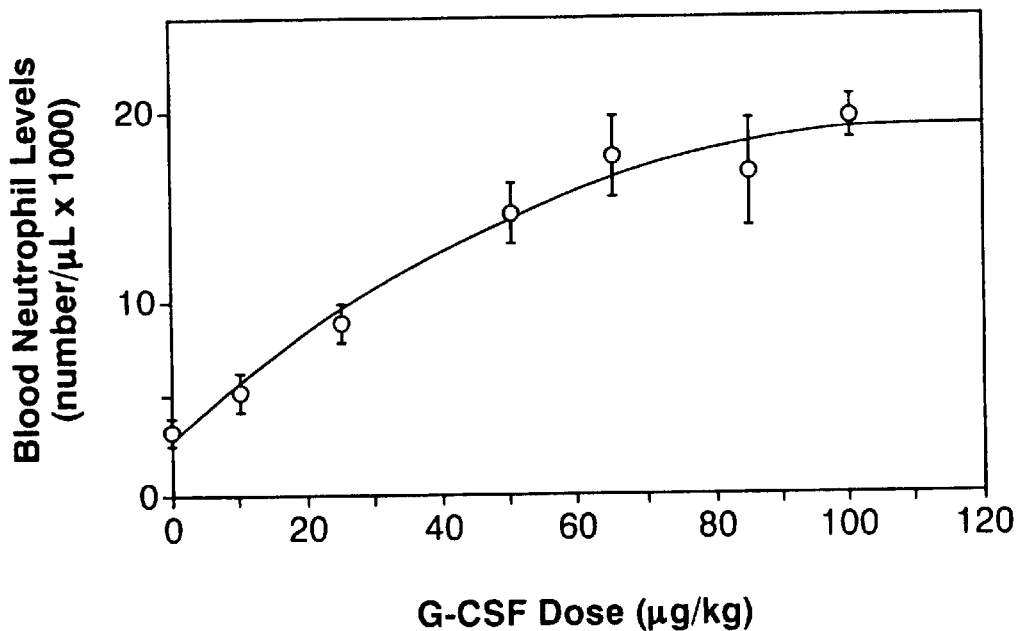

Folkesson et al., J. Appl. Physiol. 71:1106–1111 (1991) "Lung to Blood Passage of Different–sized Molecules During Lung Inflammation in the Rat".

Jones et al., JPP 40:92P (1988) "Pulmonary Absorption of Aerosolised Insulin in the Rabbit".

Jones, et al., JPP 39: 156P (1987) "Insulin Bioavailability After Pulmonary Administration to Volunteers".

Huchon et al., Amer. Rev. Resp. Dis. 131: A422 (1985) "Respiratory Epithelial Permeability to Various Molecular Weight Aerosolized Solutes".

Scharker et al., Bichem. Pharmacology 32:2599–2601 (1983) "Relation Between Molecular Weight and Pulmonary Absorption Rate of Lipid–insoluble Compounds in Neonatal and Adult Rats".

O'Hagen et al., Critical Reviews in Therapeutic Drug Cancer Systems 7:35–97 (1990) at pp. 58–59.

Francis, Focus on Growth Factors 3: 4–10 (May 1992) (published by Mediscript, Mountainview Court, Friem Barnet Lane, London N20 OLD, UK).

Malik et al., Exp. Hematol. 20: 1028–1035 (1992) "Polyethylene Glycol (PEG)–modified Granulocyte–Macrophage Colony–stimulating Factor (GM–CSF) with Conserved Biological Activity".

* cited by examiner

PULMONARY ADMINISTRATION OF GRANULOCYTE COLONY STIMULATING FACTOR

This application is a continuation-in-part of application Ser. No. 07/953,208, filed Sep. 29, 1992, now U.S. Pat. No. 5,284,656 which is a continuation of application Ser. No. 07/669,792, filed Mar. 15, 1991, now abandoned.

FIELD OF THE INVENTION

The present invention relates to the pulmonary administration of a therapeutic protein and, more particularly, to the systemic administration via the respiratory system of therapeutically effective amounts of granulocyte colony stimulating factor (G-CSF) or chemically modified G-CSF. In another aspect, the present invention relates to the pulmonary administration of a pegylated protein.

BACKGROUND OF THE INVENTION

G-CSF is a hormone-like glycoprotein which regulates hematopoiesis and is required for the clonal growth and maturation of normal hematopoietic precursor cells found in the bone marrow; Welte et al., *Proc. Natl. Acad. Sci.*, Vol. 82, pp. 1526–1530 (1985). More specifically, G-CSF, when present in low concentrations, is known to stimulate the production of neutrophil granulocytic colonies when used in vitro. G-CSF is also known to enhance neutrophil migration; Gabrilove, J., *Seminars in Hematology*, Vol. 26, No. 2, pp. 1–4 (1989). Moreover, G-CSF can significantly increase the ability of neutrophils to kill tumor cells in vitro through antibody mediated cellular cytotoxicity; Souza et al., *Science*, Vol. 232, pp. 61–65 (1986).

In humans, endogenous G-CSF is detectable in blood plasma; Jones et al., *Bailliere's Clinical Hematology*, Vol. 2, No. 1, pp.83–111. G-CSF is produced by fibroblasts, macrophages, T cells, trophoblasts, endothelial cells and epithelial cells and is the expression product of a single copy gene comprised of four exons and five introns located on chromosome seventeen. Transcription of this locus produces a mRNA species which is differentially processed, resulting in the expression of two forms of G-CSF, one version having a mature length of 177 amino acids, the other having a mature length of 174 amino acids. The form comprised of 174 amino acids has been found to have the greatest specific in vivo biological activity. G-CSF is species cross-reactive, such that when human G-CSF is administered to another mammal such as a mouse, canine or monkey, sustained neutrophil leukocytosis is elicited; Moore et al., *Proc. Natl. Acad. Sci.*, Vol. 84, pp. 7134–7138 (1987).

Human G-CSF can be obtained and purified from a number of sources. Natural human G-CSF (nhG-CSF) can be isolated from the supernatants of cultured human tumor cell lines. The development of recombinant DNA technology, see, for instance, U.S. Pat. No. 4,810,643 (Souza), incorporated herein by reference, has enabled the production of commercial scale quantities of G-CSF in glycosylated form as a product of eukaryotic host cell expression, and of G-CSF in non-glycosylated form as a product of prokaryotic host cell expression.

Chemically modified G-CSF may also be obtained in numerous ways. Chemical modification may provide additional advantages, such as increasing the stability and clearance time of the therapeutic protein. A review article describing protein modification and fusion proteins is Francis, *Focus on Growth Factors* 3: 4–10 (May 1992) (published by Mediscript, Mountview Court, Friern Barnet Lane, London N20 OLD, UK). For example, see EP 0 401 384, entitled, "*Chemically Modified Granulocyte Colony Stimulating Factor*," which describes materials and methods for preparing G-CSF to which polyethylene glycol molecules are attached. (Such modified G-CSF is referred to herein as "pegylated G-CSF" or "PEG-G-CSF."). Such chemically modified G-CSF may be obtained by modifying nhG-CSF or G-CSF obtained as a product of prokaryotic or eukaryotic host cell expression.

G-CSF has been found to be useful in the treatment of cancer, as a means of stimulating neutrophil production to compensate for hematopoietic deficits resulting from chemotherapy or radiation therapy. The effective use of G-CSF as a therapeutic agent requires that patients be administered systemic doses of the protein. Currently, parenteral administration via intravenous, intramuscular or subcutaneous injection is the preferred route of administration to humans and has heretofore appeared to be the only practical way to deliver therapeutically significant amounts of G-CSF to the bloodstream, although attempts have been made at oral delivery; see, for example, Takada et al., *Chem. Pharm. Bull.*, Vol. 37, No. 3, pp. 838–839 (1989). Pulmonary delivery of chemically modified G-CSF has not been demonstrated previously, nor has pulmonary delivery of protein to which one or more polyethylene glycol molecules has been attached.

The pulmonary delivery of relatively large molecules is not unknown, although there are only a few examples which have been quantitatively substantiated. Leuprolide acetate is a nonapeptide with luteinizing hormone releasing hormone (LHRH) agonist activity having low oral availability. Studies with animals indicate that inhalation of an aerosol formulation of leuprolide acetate results in meaningful levels in the blood; Adjei et al., Pharmaceutical Research, Vol. 7, No. 6, pp. 565–569 (1990); Adjei et al., *International Journal of Pharmaceutics*, Vol. 63, pp. 135–144 (1990).

Endothelin-1 (ET-1), a 21 amino acid vasoconstrictor peptide produced by endothelial cells, has been found to decrease arterial blood pressure when administered by aerosol to guinea pigs; Braquet et al., *Journal of Cardiovascular Pharmacology*, Vol. 13, suppl. 5, s. 143–146 (1989).

The feasibility of delivering human plasma α1-antitrypsin to the pulmonary system using aerosol administration, with some of the drug gaining access to the systemic circulation, is reported by Hubbard et al., *Annals of Internal Medicine*, Vol. III, No. 3, pp. 206–212(1989)

Pulmonary administration of α-1-proteinase inhibitor to dogs and sheep has been found to result in passage of some of that substance into the bloodstream; Smith et al., *J. Clin. Invest.*, Vol. 84, pp. 1145–1146 (1989).

Experiments with test animals have shown that recombinant human growth hormone, when delivered by aerosol, is rapidly absorbed from the lung and produces faster growth comparable to that seen with subcutaneous injection; Oswein et al., "*Aerosolization of Proteins*", Proceedings of Symposium on Respiratory Drug Delivery II, Keystone, Colo., March, 1990. Recombinant versions of the cytokines gamma interferon (IFN-γ) and tumor necrosis factor alpha (TNF-α) have also been observed in the bloodstream after aerosol administration to the lung; Debs et al., *The Journal of Immunology*, Vol. 140, pp. 3482–3488 (1988).

Pulmonary administration of pegylated proteins has not been demonstrated previously, although, as noted above, chemical modification of proteins, including pegylation, has been demonstrated for a variety of proteins, including G-CSF.

SUMMARY OF THE INVENTION

The present invention is based on the discovery that G-CSF can be administered systemically to a mammal via the pulmonary route. Typically, this is accomplished by directing a stream of a therapeutically effective amount of G-CSF into the oral or nasal cavity of the inhaling mammal. Importantly, and surprisingly, substantial amounts of G-CSF are thereby deposited in the lung and absorbed from the lung into the bloodstream, resulting in elevated blood neutrophil levels. Moreover, this is accomplished without the necessity to resort to special measures such as the use of absorption enhancing agents or protein derivatives specifically designed to improve absorption. Pulmonary administration of G-CSF thus provides an effective non-invasive alternative to the systemic delivery of G-CSF by injection.

In another aspect, the present invention is based on the discovery that chemically modified G-CSF may be absorbed from the lung into the bloodstream. In addition to the advantages of pulmonary delivery as described above, this provides additional advantages. Chemical modification may lengthen the circulation time of the protein in the body, alter immunoreactivity, reduce toxicity, alter bioactivity, and alter certain physical properties of the therapeutic peptide.

In yet another aspect, the present invention is based on the broad discovery that a protein to which a polyethylene glycol molecule has been attached may be absorbed by the lung into the bloodstream. Polyethylene glycol, or "PEG" is a hydrophilic polymer. For example, solid PEGs are insoluble in liquid paraffin, fats and fixed oils. Handbook of Pharmaceutical Excipients, (American Pharmaceutical Association and The Pharmaceutical Society of Great Britian), pages 209–213 at 210. Further, the structure of the lung is such that while gaseous exchange is facilitated, uptake of solids or liquids is not. The membrane junctions between the epithelia cells are considered tight, and as such, would not be expected to allow absorption or transfer of large hydrophilic molecules. As such, PEG is not expected to cross hydrophobic membranes to any significant degree.

The pulmonary administration of G-CSF or chemically modified G-CSF can be practiced using any purified isolated polypeptide having part or all of the primary structural conformation (i.e., continuous sequence of amino acid residues) and one or more of the biological properties of naturally occurring G-CSF. A number of publications describe methods of producing G-CSFs, including the above mentioned Souza patent and the Welte et al. and Nicola et al. articles.

In general, G-CSF useful in the practice of this invention may be a native form isolated pure from mammalian organisms or, alternatively, a product of chemical synthetic procedures or of procaryotic or eucaryotic host expression of exogenous DNA sequences obtained by genomic or cDNA cloning or by gene synthesis. Suitable procaryotic hosts include various bacterial (e.g., E. coli) cells. Suitable eucaryotic hosts include yeast (e.g., S. cerevisiae) and mammalian (e.g., Chinese hamster ovary, monkey) cells. Depending upon the host employed, the G-CSF expression product may be glycosylated with mammalian or other eucaryotic carbohydrates, or it may be non-glycosylated. The G-CSF expression product may also include an initial methionine amino acid residue (at position −1). The present invention contemplates the use of any and all such forms of G-CSF, although recombinant G-CSF, especially E. coli derived, is preferred for reasons of greatest commercial practicality.

The G-CSF to be chemically modified for use in the present invention may also be either nhG-CSF or the product of a recombinant nucleic acid process, such as prokaryotic or eukaryotic host cell expression. In general, chemical modification contemplated is the attachment of a chemical moiety to the G-CSF molecule itself, where said chemical moiety permits pulmonary administration of the chemically modified G-CSF. The attachment may be by bonding, directly to the protein or to a moiety which acts as a bridge to the active agent. Covalent bonding is preferred as the most stable for attachment. The chemical modification may contribute to the controlled, sustained or extended effect of the G-CSF. This may have the effect, for example, of controlling the amount of time the chemically modified G-CSF takes to reach the circulation. An example of a chemical modifier is polyethylene glycols, including derivatives thereof.

Contemplated for use in the practice of this invention are any chemically modified G-CSF preparations which permit efficacy upon pulmonary administration. Efficacy may be determined by known methods, as a practitioner in the art will recognize. Pegylated G-CSF, especially pegylated E. coli derived G-CSF, and more particularly, tri-tetra pegylated E. coli derived G-CSF (as described below) is preferred.

When attaching the chemical moiety to the G-CSF or other peptide, one should consider the location of the attachment. For example, attachment in a location affecting the receptor binding site, functional domains or antigenic domains may also affect the biological activity.

Contemplated for use in the practice of pulmonary administration of a pegylated protein are a variety of compositions for which pulmonary administration would be desired in pegylated form. Exemplary proteins contemplated are cytokines, including various hematopoietic factors such as G-CSF, SCF, EPO, GM-CSF, CSF-1, the interleukins such as IL-1, IL-2, IL-3, IL-4, IL-5, IL-6, IL-7, IL-8, IL-9, IL-10, IL-11 and IL-12, IGFs, M-CSF, thymosin, TNF, or LIF. Other therapeutic proteins such as interferons (alpha-, beta-, gamma- or consensus interferons) and growth factors or hormones are also useful, such as human or other animal growth hormones (for example, bovine, porcine, or chicken growth hormone), insulin, ET-1, FGF, KGF, EGF, IGF, PDGF, and α-1 antitrypsin. Protease inhibitors, such as metalloproteinase inhibitors are contemplated (such as TIMP-1, TIMP-2, or other proteinase inhibitors). Nerve growth factors are also contemplated, such as BDNF and NT3. Plasminogen activators, such as tPA, urokinase and streptokinase are also contemplated. Also contemplated are peptide portions of proteins having all or part of the primary structural conformation of the parent protein and at least one of the biological properties of the parent protein. Analogs, such as substitution or deletion analogs, or those containing altered amino acids, such as peptidomimetics are also contemplated.

Also contemplated is use of polyethylene glycol molecules with a range of molecular weights. Preferred are those polyethylene glycol molecules which act to increase the half life of the peptide, typically those PEG molecules with a molecular weight of between about 500 and about 20,000. The term "about" is used to reflect the approximate average molecular weight of a polyethylene glycol preparation, recognizing that some molecules in the preparation will weigh more, some less. Preferred are "solid" PEGs which are insoluble in fats and oils. "Solid" PEGs are generally of MW 1000 or above, although PEG 600 can be solid at ambient temperatures. Handbook of Pharmaceutical Excipients, supra, page 209, which is incorporated by reference. The PEG used in the working examples described below had a molecular weight of about 6000, and acted to increase the half life of the G-CSF used.

The polyethylene glycol molecules should be attached to the peptide with consideration of effects on functional or antigenic domains as noted above. The method for attachment of the polyethylene glycol molecules may vary, and there are a number of methods available to those skilled in the art. E.g., EP 0 401 384 (coupling PEG to G-CSF), see also, Malik et al, *Exp. Hematol.* 20: 1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydrl groups may also be used as a reactive group for attaching the polyethylene glycol molecules.

The number of polyethylene glycol molecules so attached may vary, and one skilled in the art will be able to ascertain the effect on function. As noted in more detail below, the pegylated G-CSF preferred herein is tri-tetra pegylated with PEG 6000, i.e., a G-CSF molecule having three or four PEG 6000 molecules attached.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of G-CSF. Typically, each formulation is specific to the type of device employed and may involve the use of an appropriate propellant material, in addition to the usual diluents, adjuvants and/or carriers useful in G-CSF therapy. Also, the use of liposomes, microcapsules or microspheres, inclusion complexes, or other types of carriers is contemplated. Chemically modified G-CSF may also be prepared in different formulations depending on the type of chemical modification or the type of device employed. G-CSF formulations which can be utilized in the most common types of pulmonary dispensing devices to practice this invention are now described, and the same factors should be taken into consideration when formulating chemically modified G-CSF or a pegylated protein for pulmonary administration.

Nebulizer Formulations

Formulations suitable for use with a nebulizer, either jet or ultrasonic, will typically comprise G-CSF (or chemically modified G-CSF or pegylated protein) dissolved in water at a concentration of about 0.1 to 25 mg of G-CSF (or chemically modified G-CSF or pegylated protein) per mL of solution. The formulation may also include a buffer and a simple sugar (e.g., for protein stabilization and regulation of osmotic pressure). Examples of buffers which may be used are sodium acetate, citrate and glycine. Preferably, for G-CSF formulations, the buffer will have a composition and molarity suitable to adjust the solution to a pH in the range of 3 to 4. Generally, buffer molarities of from 2 mM to 50 mM are suitable for this purpose. Examples of sugars which can be utilized are mannitol and sorbitol, usually in amounts ranging from 1% to 10% by weight of the formulation.

The nebulizer formulation may also contain a surfactant, to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001 and 4% by weight of the formulation. An especially preferred surfactant for purposes of this invention is polyoxyethylene sorbitan monooleate.

Metered Dose Inhaler Formulations

Formulations for use with a metered-dose inhaler device will generally comprise a finely divided powder containing G-CSF (or chemically modified G-CSF or a pegylated protein) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Powder Inhaler Formulations

Formulations for dispensing from a powder inhaler device will comprise a finely divided dry powder containing G-CSF (or chemically modified G-CSF or a pegylated protein) and may also include a bulking agent, such as lactose, sorbitol, sucrose, or mannitol in amounts which facilitate dispersal of the powder from the device, e.g., 50 to 90% by weight of the formulation. The G-CSF (or chemically modified G-CSF or pegylated protein) should most advantageously be prepared in particulate form with an average particle size of less than 10 $\mu$m (or microns), most preferably 0.5 to 5 $\mu$m, for most effective delivery to the distal lung.

The invention contemplates the administration of therapeutic amounts of the protein, i.e., G-CSF or chemically modified G-CSF, sufficient to achieve elevation of the neutrophil level in the systemic blood. What constitutes a therapeutically effective amount of G-CSF or chemically modified G-CSF in a particular case will depend on a variety of factors which the knowledgeable practitioner will take into account, including the normal blood neutrophil level for that subject, the severity of the condition or illness being treated, the degree of neutropenia, the physical condition of the subject, and so forth. In general, a dosage regimen will be followed such that the normal blood neutrophil level for the individual undergoing treatment is restored, at least in cases of abnormally low or depressed blood neutrophil counts. For humans, the normal blood neutrophil level is about 5000 to 6000 neutrophils per microliter of blood. Neutrophil counts below 1000 in humans are generally regarded as indicative of severe neutropenia and as placing the subject at great risk to infection. Clinical studies with cancer patients suffering from chemotherapy-induced neutropenia have shown that subcutaneous injected doses of 3–5 $\mu$g G-CSF/kg every twenty-four hours are effective in elevating acutely deficient blood neutrophil levels above 1000. Based on preliminary results with animals, described below, it is anticipated that for most mammals, including humans, the administered dose of G-CSF for pulmonary delivery (referred to here as the inhalation dose) will be about 3 to 10 times the corresponding subcutaneous dose necessary to achieve a particular blood neutrophil level.

The therapeutic dosage for chemically modified G-CSF may be ascertained taking into account the variety of factors listed above. Some chemical modification, such as pegylation, may lengthen the half-life of G-CSF in the body, and this should also be considered when ascertaining therapeutic dosage. Chemical modification may also alter immunoreactivity, reduce toxicity, alter bioactivity, and alter certain physical properties of the therapeutic protein, additional variables to consider when ascertaining therapeutic dosage of chemically modified G-CSF. Pegylated G-CSF, the chemically modified G-CSF used herein as an example, is known to have a serum half-life greater than that of non-pegylated G-CSF.

For other pegylated proteins, one skilled in the art should consider that pegylation may modify the pharmacological properties of proteins, usually extending the plasma half-life and concomitantly increasing in vivo bioactivity, and may reduce antigenicity and immunogenicity. There may also be an increase in solubility and resistance to proteolysis. For other general considerations when determining dosages, see *Remington's Pharmaceutical Sciences,* 18th Ed. 1990 (Mack Publishing Co., Easton, Pa.) Chapter 35.

As those skilled in the art will recognize, the operating conditions for delivery of a suitable inhalation dose will vary according to the type of mechanical device employed. For some aerosol delivery systems, such as nebulizers, the frequency of administration and operating period will be dictated chiefly by the amount of G-CSF or other active composition per unit volume in the aerosol. In general, the higher the concentration of protein in the nebulizer solution the shorter the operating period. Some devices such as metered dose inhalers may produce higher aerosol concentrations than others and thus will be operated for shorter periods to give the desired result.

Other devices such as powder inhalers are designed to be used until a given charge of active material is exhausted from the device. The charge loaded into the device will be formulated accordingly to contain the proper inhalation dose amount of G-CSF or other active ingredient for delivery in a single administration. See generally, *Remington's Pharmaceutical Sciences,* (18th Ed. 1990, Mack Publishing Co., Easton, Pa.) Chapter 92 for information relating to aerosol administration.

Figure 17:
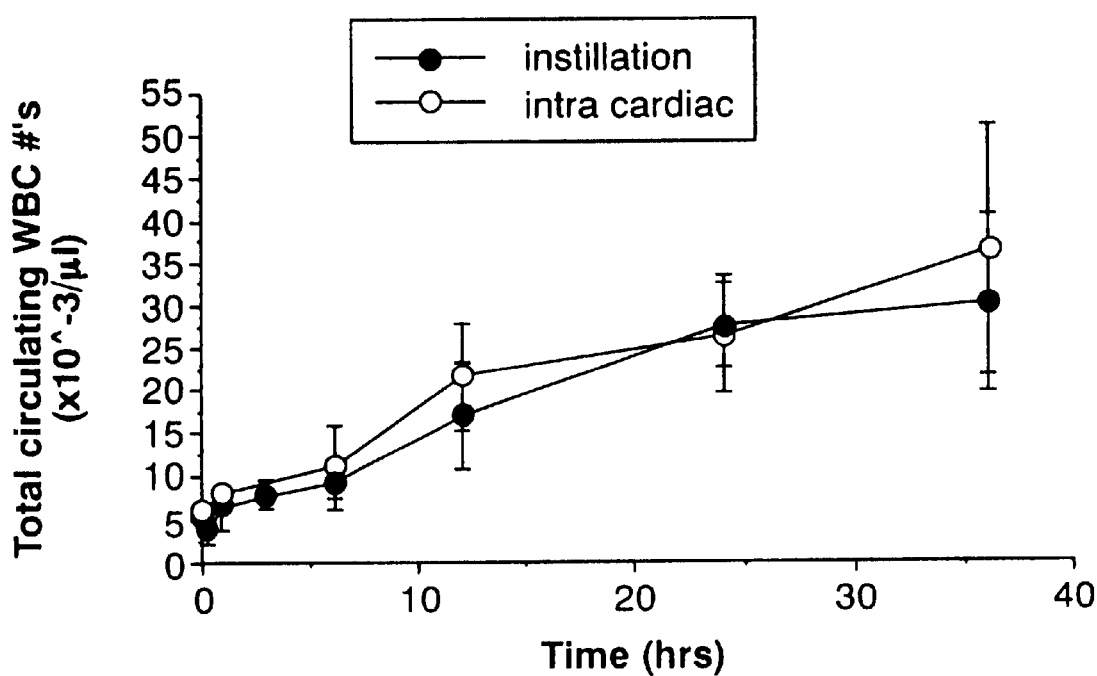

Regardless of what device is used for aerosolization, the active ingredients will be in the form of a dispersion of particles. The dispersion of particles may be in the form of liquid droplets or in the form of powder (dry or suspended). The dispersant itself, including the G-CSF, the chemically modified G-CSF, or a pegylated protein, is the population of particles which is emitted from the delivery device for deposition within the lung. As set forth above, an average particle size (mass median diameter) of less than 10 $\mu$m (or microns), most preferably 0.5 to 5 $\mu$m, is used for most effective delivery to the distal lung. For example, the dispersion of particles may consist essentially of pegylated protein, such as the pegylated G-CSF described herein, in a pharmaceutically acceptable carrier.

While G-CSF has been found useful in treating neutrophil-deficient conditions such as chemotherapy related neutropenia, G-CSF is expected to also be effective in combating infections and in treating other conditions or illnesses where blood neutrophil levels elevated above the norm can result in medical benefit. As further studies are conducted, information will emerge regarding appropriate dosage levels for the administration of G-CSF in these latter cases. Also, as further studies are accomplished using pegylated G-CSF, it is expected that appropriate formulations and dosages will be ascertained for the same uses. It is expected that the present invention will be applicable as a non-invasive alternative in most instances where G-CSF (or chemically modified G-CSF or a pegylated proteins) is administered therapeutically by injection.

BRIEF DESCRIPTION OF THE DRAWINGS

FIG. 1 is a graphical depiction of the effect of subcutaneously administered rhG-CSF on blood neutrophil levels in hamsters.

FIG. 2 is a bar graph of the blood neutrophil levels in hamsters following exposure to aerosols generated from either an Acorn II nebulizer or an Ultravent nebulizer, using different concentrations of rhG-CSF in aqueous solution.

FIG. 3 depicts a comparison of blood neutrophil levels resulting from subcutaneous and aerosol administration of rhG-CSF.

FIG. 4 is a graph of the white blood cell count at time intervals 0–6 hours after pulmonary administration of 50 $\mu$g of pegylated G-CSF.

FIG. 5 is a bar graph of the effects of pegylated G-CSF on circulating cell differentials up to six hours after intratracheal administration.

FIG. 6 is a graph of the circulating neutrophil and macrophage numbers from zero to six hours after intratracheal instillation of 50 $\mu$g pegylated G-CSF.

FIG. 7 is a graph of the circulating white blood cell counts after intratracheal instillation of 50 $\mu$g pegylated G-CSF over 5 days.

FIG. 8 is a graph of the weight change of animals after a single intratracheal dose of 50 $\mu$g non-pegylated G-CSF.

FIG. 9 is a graph of the differential cell types in circulation after intratracheal instillation of 500 $\mu$g/kg pegylated G-CSF.

FIG. 10 is a graph of cell types in bronchoaveolar lavage ("BAL") after intratracheal instillation of 500 $\mu$g/kg pegylated G-CSF.

FIG. 11 is a bar graph illustrating the effect on white blood cell count number using an inhaled anesthetic vs. using no inhaled anesthetic 24 hours after intratracheal instillation of 50 $\mu$g non-pegylated G-CSF.

FIG. 12 is a bar graph of neutrophils in BAL after intratracheal instillation of 50 $\mu$g non-pegylated G-CSF.

FIG. 13 is a graph of the relative concentrations of pegylated G-CSF and non-pegylated G-CSF in BAL and serum after intratracheal instillation as determined by immunoassay.

FIG. 14 is a graph of the logarithmic transformation of the rate that either pegylated or non-pegylated G-CSF is absorbed from the lungs as presented in micrograms present in BAL vs. time, with absorption rate constants ((ka)/hr)).

FIG. 15 is a graph of the dose response curve (logarithmic) to instilled and subcutaneous injection tri-tetra pegylated G-CSF.

FIG. 16 is a graph of the increase in circulating white blood cell counts after a single intra-cardiac injection of 500 $\mu$g/kg G-CSF tri-tetra pegylated G-CSF or HCl vehicle.

FIG. 17 is a graph of the comparison of the white blood cell counts after the intratracheal instillation or intra-cardiac injection of 500 µg/kg pegylated G-CSF.

Figure 18:
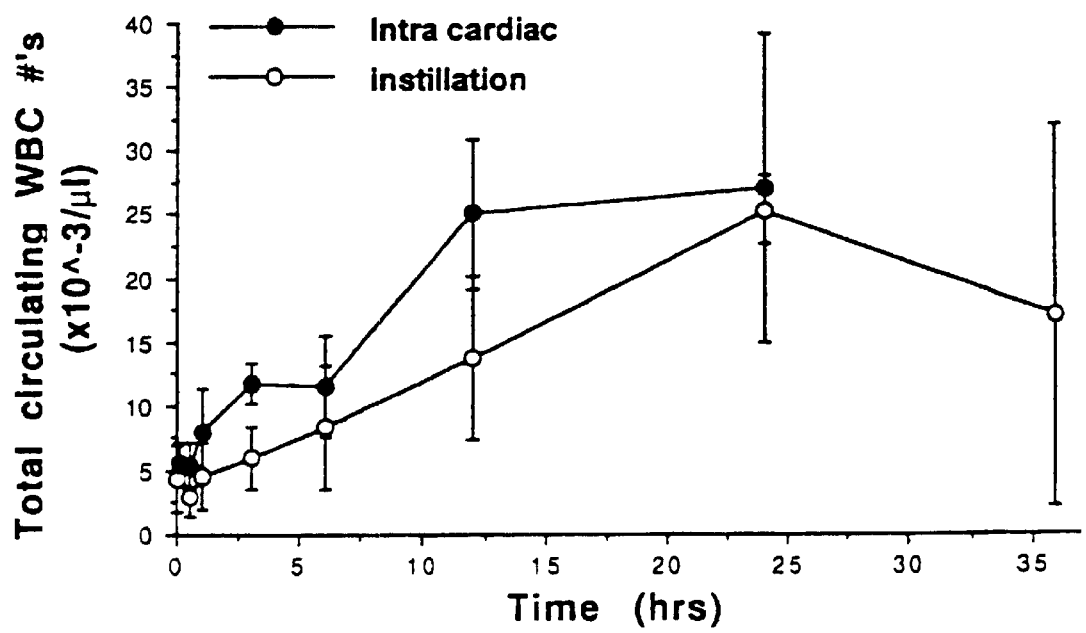

FIG. 18 is a graph of the comparison of white blood cell counts after the intratracheal instillation or intra-cardiac injection of 500 µg/kg non-pegylated G-CSF.

DETAILED DESCRIPTION

Figure 7:
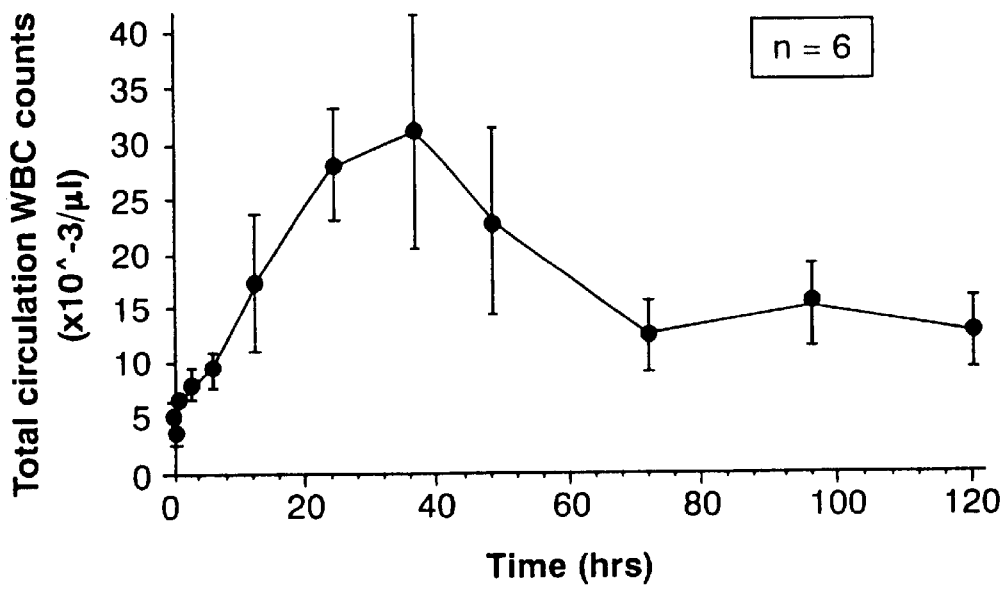

As mentioned, parenteral administration of G-CSF is known to cause an increase in the number of neutrophils in the peripheral blood. Studies were performed to demonstrate that inhalation of an aerosol of recombinant human G-CSF (rhG-CSF) also causes an increase in the number of blood neutrophils. The rhG-CSF employed was an *E. coli* derived recombinant expression product having the amino acid sequence shown in FIG. 7 of the aforementioned Souza patent comprising the entire hG-CSF polypeptide with an amino terminal methionine group. It can be made by use of the same procedure described therein.

The pulmonary administration of chemically modified G-CSF is also described herein, using rhG-CSF (as described above) to which polyethylene glycol molecules have been attached. The use of pegylated G-CSF for pulmonary administration demonstrates that chemically modified G-CSF, and, in another respect, a pegylated protein, can be absorbed through the lung.

Aerosol Administration of rhG-CSF

EXAMPLE 1

Subcutaneous Administration to Hamsters

Initial experiments were performed to measure the change in the number of neutrophils in the blood of 4–6 week old male Golden Syrian hamsters (Charles River Laboratories, Wilmington, Mass.), following subcutaneous administration of various doses of rhG-CSF. The rhG-CSF was prepared as a 4 mg/ml solution in sterile distilled water, diluted in sterile 0.9% saline solution, and different volumes were immediately injected subcutaneously in the lower back of hamsters in test groups of 3 to 5 animals. Twenty-four hours later, blood was collected from each hamster by cardiac puncture under halothane anesthesia. The number of neutrophils in the blood was determined by performing differential and complete blood cell counts. Results of these experiments, shown in FIG. 1, indicate a dose-dependent increase in the number of neutrophils twenty-four hours after injection of rhG-CSF is observed for doses up to approximately 100 micrograms per kilogram of body weight (µg/kg). The dose response curve appeared to level off at greater doses.

EXAMPLE 2

Aerosol Characterization and Administration

Inhalation exposures to aerosols containing rhG-CSF were conducted using a small animal exposure chamber manufactured by In-Tox Products (Albuquerque, N. Mex.). Only the central 12 ports in the animal chamber were used; the peripheral ports in the aerosol distribution manifold in the animal chamber were sealed. With this modification to the chamber, the air supplied by a nebulizer was adequate to maintain 10 hamsters during an exposure. Filter samples were taken from one of the animal ports and from the air exhaust line to measure the aerosol concentration in the exposure chamber. The aerosol was sampled from the remaining available animal port, and particle size distribution measurements with a QCM (quartz crystal monitor) cascade impactor (California Instruments, Inc., Sierra Madre, Calif.) were taken periodically throughout an exposure. This cascade impactor draws only 240 mL/min, which allows the particle size distribution of the aerosol to be measured without disturbing the airflow pattern in the exposure chamber.

Prior to conducting the animal exposure studies, the aerosol concentration and particle size distribution of aerosols generated from a 20 mg/mL albumin solution, using either the Ultravent nebulizer or the Acorn II nebulizer (both jet type), were measured in the exposure chamber. Table 1 shows the particle size distribution and the average albumin concentration in the aerosol measured at two locations (nose and outlet) in the chamber. The Ultravent produced an aerosol having much smaller particles than the Acorn II, but the Acorn II produced a more concentrated aerosol. It was found that the two nebulizers delivered a roughly equivalent amount of protein to an animal when the devices were operated until the initial charge of 5 mL was exhausted and aerosol generation became erratic (10 or 15 minutes for the Acorn II depending on the operating air flow rate, and 20 minutes for the Ultravent).

TABLE 1

AEROSOL CONCENTRATION AND INHALATION DOSE
ESTIMATES FOR TWO JET NEBULIZERS USING A
20 mg/ml ALBUMIN SOLUTION

| Nebulizer | Aerosol Conc. µg/L ± SEM | MMAD (µm)* GSD | Period (minute) | Delivered Dose µg/L ± SEM |
|---|---|---|---|---|
| Ultravent 10 L/min | outlet 126 ± 13 | 0.93 | 20 | 76 ± 8 |
|  | nose 141 ± 17 | 3.6 | 20 | 85 ± 10 |
| Acorn II 8 L/min | outlet 239 ± 48 | 2.8 | 15 | 107 ± 29 |
|  | nose 141 ± 17 | 2.9 | 15 | 133 ± 3 |
| 10 L/min | outlet 362 | — | 10 | 109 |

*MMAD = Mass median aerodynamic diameter; GSD = Geometric standard deviation; SEM = standard error of the mean of three determinations An estimate of the amount of G-CSF delivered via aerosol to a hamster during an inhalation exposure from a nebulizer was determined from the following expression:

$$D = \eta V C \Delta t$$

where D is the inhalation dose, $\eta$ is the fractional deposition, V is the ventilation rate, C is the aerosol concentration, and $\Delta t$ is the period of administration. By using the measured aerosol concentration (C) and operating period ($\Delta t$) of the nebulizer, along with the resting ventilation rate (V) for a mature hamster of 30 mL/min and a fractional deposition ($\eta$) of 0.5, it was determined that G-CSF concentrations of between 5 mg/mL and 10 mg/mL of nebulizer solution would result in an inhalation dose of 100 µg/kg (e.g., 10 µg for a 100 g hamster). This was the dose estimated to produce a maximal neutrophil response via pulmonary delivery.

EXAMPLE 3

Aerosol Administration of G-CSF to Hamsters

The solutions used to conduct aerosol exposures were prepared by reconstituting lyophilized rhG-CSF in sterile distilled water containing 1 mg/mL of the nonionic surfactant polyoxyethylenesorbitan monooleate. The solutions used in the nebulizer to generate the exposure aerosols were prepared with G-CSF in concentrations ranging from 1 to 15 mg/mL.

Groups of ten hamsters (mature, male Golden Syrian) were exposed to aerosols containing rhG-CSF. The hamsters were placed in restraining tubes and allowed to acclimate for approximately 5 minutes. The tubes were then inserted into the exposure chamber and the aerosol exposure was initiated. Following exposure, the hamsters were returned to their cages and given free access to food and water. Blood samples were taken 24 hours after exposure, and the blood neutrophil concentration was determined by the same procedure used to evaluate the blood samples following subcutaneous injection.

The aerosol concentration and particle size distribution were measured during each exposure. The G-CSF dose was varied from one exposure to another by using different concentrations of G-CSF in the nebulizer solution.

Figure 2:
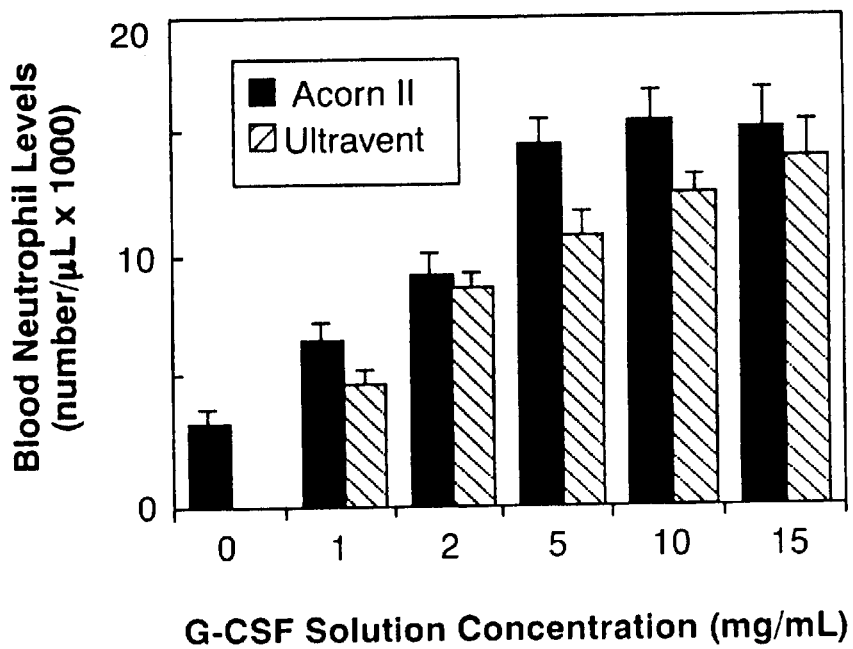

Hamsters exposed to aerosols containing G-CSF were found to have elevated neutrophil concentrations when compared to untreated animals and animals exposed to an aerosol containing only water and surfactant (polyoxyethylene sorbitum monooleate). FIG. 2 shows the increase in neutrophil counts observed in animals exposed to aerosols generated from rhG-CSF nebulizer solutions ranging in concentration as described. As can be seen, the circulating neutrophil levels obtained from G-CSF aerosol exposure, even with as low a concentration as 1 mg/mL of G-CSF (using the Ultravent nebulizer), were significantly higher ($p<0.05$) than the group exposed to an aerosol without G-CSF. The statistical significance of the increase in neutrophil levels over the control was $p<0.001$ for all the other groups. The increase in blood neutrophil levels correlated with increasing G-CSF concentration in the nebulizer solution up to a concentration of 5 mg/mL. A maximum response of 15,000 neutrophils per $\mu$L of blood was observed with the more concentrated G-CSF nebulizer solutions, similar to the maximum obtained with subcutaneous injection of doses greater than 50 $\mu$g/kg. There was virtually no difference in neutrophil response obtained with the two nebulizers using lower G-CSF solution concentrations, e.g., below 5 mg/mL. For G-CSF solution concentrations greater than 5 mg/mL, the Acorn II nebulizer produced a greater increase in neutrophil response than the Ultravent.

An inhalation exposure to an aerosol generated from a 5 mg/mL G-CSF solution that did not contain surfactant produced a neutrophil response (9,910±960 neutrophils/$\mu$L) in hamsters not significantly different from that obtained with either a 50 $\mu$g/kg subcutaneous injection containing surfactant (10,935±1,390 neutrophils/$\mu$L) or a 50 $\mu$g/kg subcutaneous injection prepared from the solution lacking surfactant (10,270±430 neutrophils/$\mu$L). These values are reported as the mean and standard error of ten animals for the aerosol tests and five animals for the injections. From this experiment, it was concluded that the surfactant was not a necessary component of the aqueous aerosol formulation for G-CSF.

EXAMPLE 4

Fractional Deposition of G-CSF Aerosol in Hamster Lungs

The dose delivered to the animal during an exposure was estimated in order to ascertain whether therapeutic amounts of G-CSF can be effectively and economically delivered via the lung. The delivered or deposited dose is the product of the amount of drug the animal inhales and the efficiency (fractional deposition) with which the aerosol particles deposit in the lung. The latter was determined by measurement of the amount of G-CSF recovered from the hamster lungs following aerosol exposure.

G-CSF deposited in the lungs was measured in two groups of four animals exposed to aerosols generated with the Acorn II nebulizer. Immediately following aerosol exposure, the whole lungs of four hamsters were removed, placed into glass tissue grinders containing 3 mL of cold physiological buffered saline, and homogenized. The homogenate was centrifuged twice, and the final supernatent was transferred to a clean tube and assayed for G-CSF using radioimmunoassay (Amgen Inc., Thousand Oaks, Calif.). In control experiments using this procedure, it was determined that 75% of the G-CSF could be recovered from samples of lung homogenate spiked with a known amount of G-CSF. All measurements of G-CSF in the lungs following aerosol exposure were corrected for this fractional recovery of G-CSF from lung tissue.

An average of 3.1±0.3 $\mu$g of G-CSF was deposited in the lung in the group of animals exposed for 11 minutes to an aerosol generated from a 5 mg/mL solution of the protein. An average of 20.0±4.0 $\mu$g of G-CSF was deposited in the animal group exposed for 11 minutes to an aerosol generated from a 20 mg/mL solution. Based on the concentration of G-CSF in the aerosol measured during the exposure and the resting ventilation rate (30 mL/min), the animals in the 5-mg/mL group inhaled 22 $\mu$g of G-CSF (68 $\mu$g/L×0.030 L/min×11 min), and the 20-mg/mL group inhaled 69 $\mu$g of G-CSF (208 $\mu$g/L×0.030 L/min×11 min) over an exposure period. Using the amounts of G-CSF inhaled and the amounts recovered from the lung, the deposition efficiency (fractional deposition×100) in the lung was estimated to be 14% for the 5-mg/mL group and 29% for the 20-mg/mL group.

The fractional deposition determined from the G-CSF measured in the lungs following aerosol exposure was then used to estimate the G-CSF dose administered by aerosol, in order to relate the increase in the neutrophil concentration to the aerosol dose.

Table 2 contains the inhaled and deposited doses estimated for the aerosol exposures using various concentrations of G-CSF in the nebulizer solution. The G-CSF aerosol concentration was measured gravimetrically from a filter sample collected during the exposure and the weight was corrected for the proportion of surfactant (1 mg/mL) to G-CSF in solution. The inhaled dose was calculated from the aerosol concentration, the resting ventilation rate (30 mL/min), and the exposure period (11 minutes for the Acorn II and 20 minutes for the Ultravent). The deposited dose was calculated from the inhaled dose and the measured fractional deposition (0.29).

TABLE 2

THE ESTIMATES OF G-CSF DELIVERED
TO THE LUNG DURING AEROSOL EXPOSURES

| Solution Conc (mg/ml) | [C]* ($\mu$g/L) | Inhaled Dose ($\mu$g) | Deposited dose ($\mu$g) | Mean Body weight (g) | Estimated Dose/Body Wt. ($\mu$g/kg) |
|---|---|---|---|---|---|
| Acorn II Nebulizer | | | | | |
| 1 | 8 | 2.6 | 0.75 | 66.7 | 11 |
| 2 | 10 | 3.3 | 0.96 | 76.3 | 13 |
| 5 | 73 | 24 | 7.0 | 92.2 | 76 |
| 10 | 109 | 36 | 10 | 83.3 | 125 |
| 15 | 188 | 62 | 18 | 86.1 | 209 |
| Ultravent Nebulizer | | | | | |
| 1 | 2.5 | 1.5 | 0.44 | 63.3 | 6.9 |
| 2 | 2.7 | 1.6 | 0.46 | 77.1 | 6.1 |
| 5 | 33 | 20 | 5.7 | 91.2 | 63 |
| 10 | 41 | 25 | 7.1 | 84.8 | 84 |
| 15 | 38 | 23 | 6.6 | 81.5 | 81 |

Figure 3:
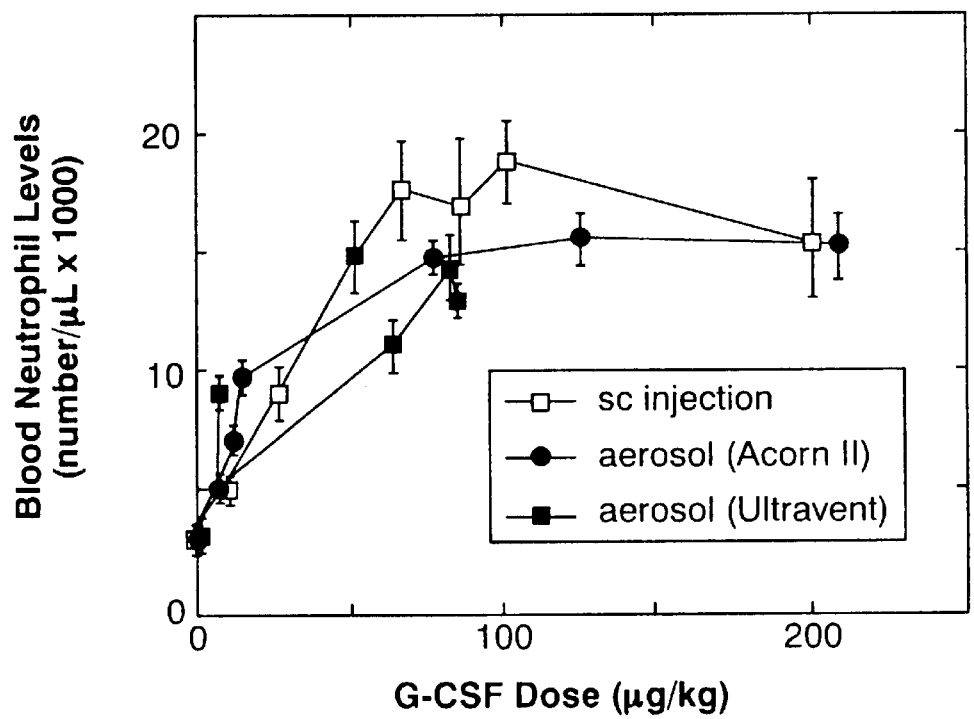

FIG. 3 shows the neutrophil response following subcutaneous injection and the aerosol administration of G-CSF for the dose levels calculated above. Comparing the neutrophil response obtained with an aerosol to that obtained by subcutaneous injection shows that, for the therapeutically important dose range of 1 to 100 µg/kg, the deposited dose is approximately equivalent to an injection.

While this invention has been specifically illustrated with regard to the use of aerosolized solutions and nebulizers, it is to be understood that any conventional means suitable for pulmonary delivery of a biological material may be employed to administer G-CSF in accordance with this invention. Indeed, there may be instances where a metered dose inhaler, or powder inhaler, or other device is preferable or best suits particular requirements. The foregoing description provides guidance as to the use of some of those devices. The application of still others is within the abilities of the skilled practitioner. Thus, this invention should not be viewed as being limited to practice by application of only the particular embodiments described.

Examples Using Chemically Modified G-CSF

Examples 5–8 below demonstrate that chemically modified G-CSF may also be administered systemically, with biological activity in vivo equaling or exceeding the efficacy of non-pegylated G-CSF. In mammals, pegylated G-CSF not only caused an increase in total white blood cell count, but also the production of a greater number of white blood cells than similar administration of non-pegylated G-CSF. Furthermore, the numbers of white blood cells were sustained for a longer period with pegylated G-CSF, than for non-pegylated G-CSF.

The examples using pegylated G-CSF also demonstrate that pulmonary administration is unexpectedly efficacious for pegylated proteins.

In Example 5 pulmonary administration of pegylated G-CSF via intratracheal instillation was compared to pulmonary administration of non-pegylated recombinant G-CSF. Two observations are notable: (a) the pegylated G-CSF was absorbed from the lungs to the blood stream, and remained in the blood stream longer than non-pegylated G-CSF; and (b) overtime, the increase in total white blood cells was higher and was maintained longer with the pegylated G-CSF than with non-pegylated G-CSF.

In Example 6, immunoassays were performed to determine how long G-CSF is detected in serum when administered to the lungs in pegylated vs. non-pegylated form. These data indicate that pegylated G-CSF transfers out of the lung more slowly than non-pegylated G-CSF, and reaches a peak serum concentration approximately 4 hours after non-pegylated G-CSF.

In Example 7, a dose ranging study compares pulmonary administration of pegylated G-CSF to sub-cutaneous ("sc") injection of pegylated G-CSF. The results (in terms of biological activity) were similar whether the pegylated G-CSF was instilled (pulmonary administration) or injection directly into the blood stream. This demonstrates further that pegylation does not prevent the G-CSF from absorbing through the lungs and having biological effect.

In Example 8, intra-cardiac pulmonary administration was compared to intratracheal pulmonary administration in terms of the number of total circulating white blood cells, with the following observations:

(a) for intra-cardiac administration of both G-CSF and pegylated G-CSF, the results are similar in terms of white blood cell count and rate of white blood cell count increase; and, (b) for pegylated G-CSF alone, comparing intra-cardiac administration vs. intratracheal administration, the results are similar in terms of white blood cell count and rate of increase.

Below, the materials and methods used in examples 5–8 are first set forth. The results follow.

Materials and Methods

A. Preparation of Recombinant Human met-G-CSF

Recombinant human met-G-CSF was prepared as described above according to methods in the Souza patent. The rhG-CSF employed was an *E. coli* derived recombinant expression product having the amino acid sequence shown in FIG. 7 of the Souza patent (U.S. Pat. No. 4,810,643 referenced above), comprising the entire hG-CSF polypeptide with an amino terminal methionine group.

B. Preparation of Chemically Modified G-CSF

Recombinant human met-G-CSF with three or four polyethylene glycol molecules attached, referred to herein as tri-tetra pegylated G-CSF, was used in the examples using pegylated G-CSF. Attachment was accomplished via the reactive amino groups. The mean molecular weight of the pegylated G-CSF was between about 36,500 Daltons and about 42,500 Daltons, with the molecular weight of the polyethylene glycol chains being about 6000 Daltons each. A small portion of the pegylated G-CSF may have been penta-pegylated, but this portion was negligible.

The following method was used to prepare the tri-tetra peglyated G-CSF used in the studies described herein:

One gram of recombinant human met-G-CSF, (prepared by the above method) was treated with a 15 fold molar excess of SCM-MPEG (N-hydroxy succinimidyl esters of carboxymethyl methoxy polyethylene glycol) to produce predominately tri-tetra-pegylated G-CSF. The bulk formulated G-CSF was buffer exchanged with pH 4.0 Water-for-injection ("WFI"), (Baxter, Deerfield, Ill.) and concentrated to 12.5 mg/ml. It was then diluted 1.25 fold with 500 mM Bicine, pH8, to give G-CSF (10 mg/ml) in 100 $\mu$M Bicine. The G-CSF solution was added to solid SCM-MPEG powder. After reacting for 1 hour, the mixture was diluted 5× with WFI and the pH was adjusted to 4.0 with 1N HCl.

The reaction mixture was applied to a 350 ml column of Toyopearl SP550c (TosoHaas, Philadelphia, Pa.) which had been equilibrated with 20 mM NaOAc, pH 4.0. The reaction by-products, n-hydroxysuccinimide (NHS) and unreacted PEG, did not bind to the column. The column was washed with 3 column volumes of equilibration buffer, after which PEG-G-CSF was eluted with 4 column volumes of 350 mM NaCl in 20 MM NaOAc, pH 4.0. Any unreacted G-CSF was eluted with 1M NaCl.

All of the protein containing fractions eluted with 350 mM NaCl were pooled. PEG-G-CSF was concentrated, buffer exchanged into standard G-CSF buffer (1 mM HCL in water) and adjusted to 1.0 mg/ml. The bulk was sterile filtered and stored in vials, 2 ml/vial, at a concentration of 1.0 mg/ml.

C. Procedure For Pulmonary Administration of Pegylated G-CSF: Instillation

In the following examples using pegylated G-CSF, pulmonary administration was accomplished by injection of appropriate dosages into the trachea of hamsters, a process referred to herein as instillation. The instillation procedure was used in order to facilitate dosage quantification. Aerosol administration, or other forms of pulmonary administration are also applicable for chemically modified G-CSF or pegylated proteins. All animals were treated according to applicable laws and regulations for the handling of research animals.

Male golden Syrian hamsters, approximately 100 g, were anesthetized and weighed. Anesthetized animals were placed face up on a slanted board (about a 60 degree angle), and supported to expose the throat. A fiber optic lamp was positioned externally directly adjacent to the throat such that the light emerging from the trachea could be observed through the mouth and the opening of the larynx thus distinguished from the esophagus.

A 1 ml dosing syringe containing 100 µl of G-CSF or pegylated G-CSF was attached to a 4 inch 20 G pipetting needle. This, in turn, was sheathed by a 16 G blunt nosed needle connected to a 5 ml syringe and withdrawn to 2 ml. The purpose of the sheath was to help prevent backflushing of the dose during instillation.

The dosing needle so sheathed was passed through the mouth and approximately 1.5 cm into the trachea. Positioning within the trachea was determined by "feeling" the tracheal cartilage with the edge of the dosing needle. Once in place, the syringe containing the dose (and also the air) was injected into the lungs. The needle was removed and the animals were left in place for several seconds to help prevent them from expectorating the dose. The animal was then removed and allowed to recover before returning to the cage.

Exact dosages were determined by reweighing the dosing needle (on a 4 decimal place balance) after instillation.

D. Ascertaining Blood Cell Counts/Differentials

The biological activity of pegylated G-CSF was determined by measurement of its effect on both the white blood cell counts and on percentages of different cell types present at defined time points. Total white blood cell count ("WBC"), polymorphonuclear leukocytes ("pmns" i.e., neutrophils), macrophages ("macs"), monocytes ("monos"), lymphocytes ("lymph") and eosinophils ("eos") were variously ascertained and counted. The samples were collected and analyzed by the following methods.

Blood Samples: At a fixed period of time after administration, hamsters were reweighed and then sacrificed by $CO_2$ asphyxiation. Immediately after death, blood samples were removed via cardiac puncture. Half milliter samples were used for immunoassays, (Example 6, below), to determine relative amounts of pegylated or non-pegylated G-CSF. For blood smears and total white blood cell counts, 0.5 ml samples were placed in tubes containing 0.1 ml of 3% w/v EDTA and mixed.

Lavage: Lavage, the washing and removal of lung fluid, (or bronchoaveolar lavage ("BAL") fluid), was performed in order to ascertain the degree of biological response within the lung. This was performed using 12×3 ml washes with phosphate buffered saline (pH 7.2). A small slit was made in the trachea at the level of the fifth tracheal cartilage below the crycoid cartilage such that 3 cm of an 18 G polyethylene tubing ring could be inserted. The leading edge of the tubing was inserted 1.5 cm into the trachea and tied-off with silk.

For washing, a 5 ml glass syringe containing 3 ml of PBS, attached to a 19 G blunt nosed needle was inserted into the cannula. The PBS was injected slowly into the lungs while massaging the throat. The lung fluid was then withdrawn while continuing the massage. This process was repeated 12 times.

The first 6 ml of lavage fluid was used for immunoassay of protein levels. The fluid was centrifuged at 300× g for 10 minutes, and the supernatant was withdrawn. The cells were resuspended in 0.5 ml PBS and added to the remaining 30 ml of lavage fluid. Total cell counts in the lavage fluid were measured using a hemocytometer as well as by Coulter Counter ("coulter"). To determine the differential counts, a dilute cell suspension was concentrated by centrifugation on a glass slide (Cytospin II™, Shandon Company, Pittsburgh, Pa.) and the fraction of cell types were measured by using light microscopy to count and differentiate the observed cells.

E. Procedure for Dose-Ranging Example Involving Sub-Cutaneous Administration

For Example 7 below, involving sub-cutaneous injection, 100 µl of tri-tetra pegylated G-CSF in 1 mM HCl was either instilled or injected sub-cutaneous into the lower backs of male, golden Syrian hamsters. Doses of 0.1 (six animals), 1 (six animals), 10 (nine animals), 50 (six animals), and 100 (nine animals) µg/kg were administered after anesthetization with Metafane, followed by intra-peritoneal injection of 0.4–0.5 ml of 10 mg/ml Brevital®. Animals were found to be awake and mobile 5–10 minutes after anesthetization.

Pulmonary administration via instillation was performed as described above.

F. Procedure for Intra-Cardiac Comparison Example

For Example 8 below, involving intra-cardiac administration, male golden Syrian hamsters were dosed via intra-cardiac puncture with 500 µg/kg G-CSF or tri-tetera pegylated G-CSF. In order to find the correct position of the heart on the hamster, the syringe plunger (27 G syringe needle) was withdrawn slightly once the needle was injected. The presence of back-flushed blood indicated that one of the ventricles had be en successfully penetrated.

After injection, the animals injected with non-pegylated G-CSF were sacrificed at 0.1, 0.5, 1, 3, 6, 12 and 24 hours (five animals for each time period). Animals injected with pegylated G-CSF were sacrificed at 0.1, 1, 6, 12, 24 and 36 hours (five animals at each time period). Animals injected with 100 µl of 1 mM HCL were also sacrificed at each time point (three animals for each time period).

Cell counting and differentiation was determined as above, with 0.5 ml samples removed. From these cohorts, further 1 ml samples were taken and the serum was then assayed for the presence of the G-CSF and pegylated G-CSF.

G. Procedure for Immunoassay of Serum Levels of G-CSF or Pegylated G-CSF

As indicated above, serum samples were obtained with the hamsters used in the intra-cardiac study above (injected with either pegylated or non-pegylated G-CSF). To ascertain the length of time pegylated G-CSF vs. non-pegylated G-CSF remained in the blood, the serum samples collected at various time intervals were examined for the presence and amount of G-CSF antigen.

The immunoassay was performed using a kit obtained from R & D Systems, (Indianapolis, Ind.) according to the instructions, which are herein incorporated by reference. The results presented herein are shown as relative concentrations at various time intervals, rather than as absolute values, due to limitations on assay sensitivity when the pegylated material was used.

Pegylated G-CSF Studies

EXAMPLE 5

Pulmonary Administration of Pegylated G-CSF By Intratracheal Instillation

Two studies were done to ascertain the effects of pulmonary administration of pegylated G-CSF, a 6-hour study and a longer, 5-day time course. Controls were also performed using single doses of instilled water, HCl, and G-CSF (non-pegylated) dissolved in water.

1. 6-Hour Study

The 6 hour study demonstrates that pegylated G-CSF is absorbed from the lung into the bloodstream.

Hamsters were instilled according to the above-described protocols with a 50 µg nominal dose of tri-tetra pegylated G-CSF and sacrificed at the time points of 0.1, 0.5, 1, 3, and 6 hours (6 animals for each time point). Blood and BAL samples were removed for WBC counts, immunoassay and differential determination. (Immunoassay data are presented in Example 6, below).

Figure 4:
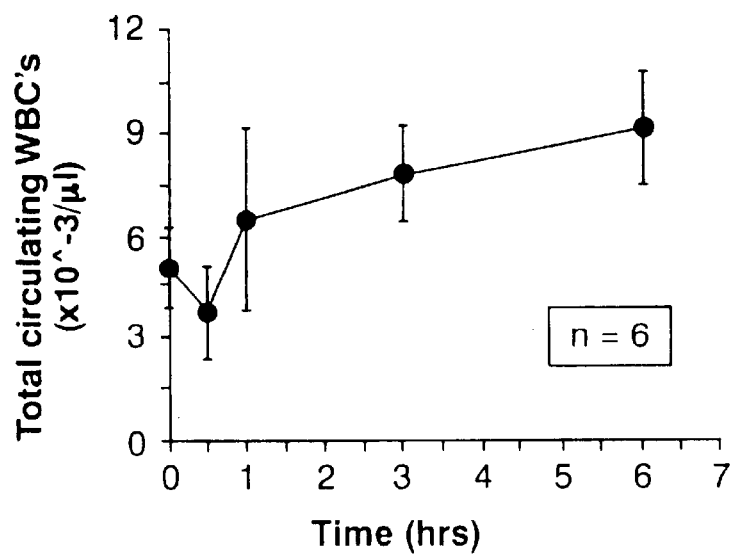

Results:

WBC: These data are presented in Table 3 (below), and plotted in FIG. 4. There is an apparent rise in the circulating WBCs between 3 and 6 hours after instillation.

TABLE 3

WHITE BLOOD CELL COUNT AFTER ADMINISTRATION OF PEGYLATED G-CSF

| | Time-Hours | | | | | | | | | | |
|---|---|---|---|---|---|---|---|---|---|---|---|
| Sample Number | 0 | 0.5 | 1.0 | 3.0 | 6.0 | 12.0 | 24.0 | 36.0 | 48.0 | 72.0 | 96.0 | 120.0 |
| Average* | 5.0 | 3.7 | 6.5 | 7.9 | 9.3 | 17.3 | 28.33 | 31.2 | 23.2 | 12.8 | 15.8 | 13.3 |
| Standard Deviation | 1.2 | 1.4 | 2.8 | 1.4 | 1.7 | 6.3 | 5.0 | 10.5 | 8.7 | 3.4 | 3.9 | 2.3 |

*Average of six samples.

Figure 5:
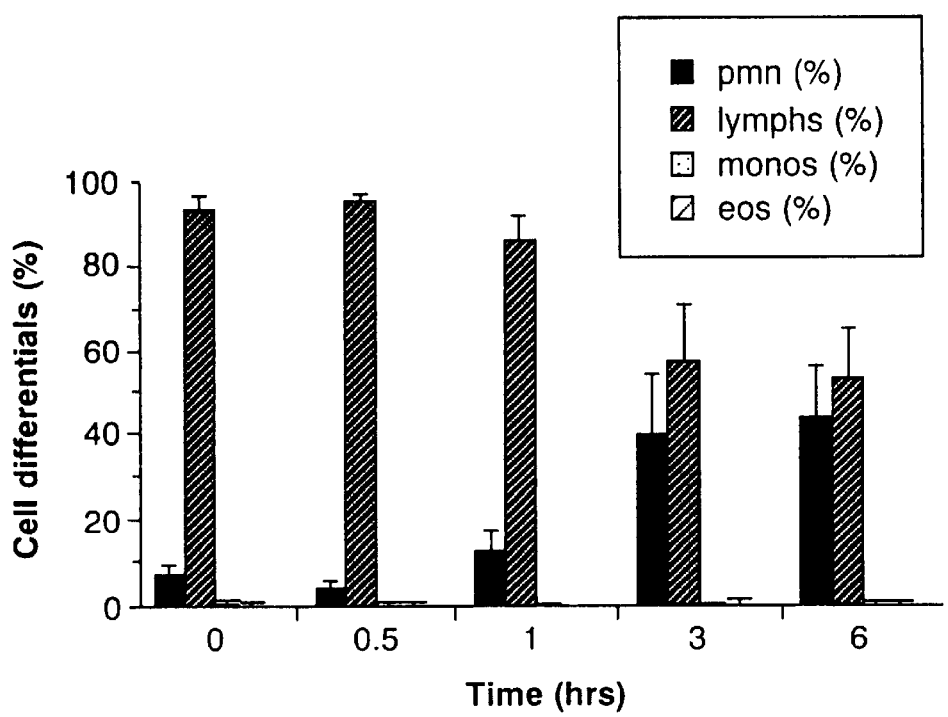

Differential cell counts: These data are presented in Table 4, and FIG. 5. A significant increase in the fraction of neutrophils (as ascertained by polymorphonuclear leukocytes or "pmns") is seen at the 3 and 6 hour time points.

TABLE 4

DIFFERENTIAL CELL COUNTS

| Hrs | | PMNs | LYMPHS | MONOS | EOS |
|---|---|---|---|---|---|
| 0 | Avg (6 Samples) | 6.0 | 93.0 | 0.2 | 0.2 |
|   | Std. Dev. | 2.7 | 3.4 | 0.4 | 0.4 |
| 0.5 | Avg (6 Samples) | 3.7 | 96.0 | 0.3 | 0.2 |
|   | Std. Dev. | 1.6 | 1.8 | 0.5 | 0.4 |
| 1.0 | Avg (6 Samples) | 12.5 | 87.3 | 0.2 | 0 |
|   | Std. Dev. | 5.4 | 5.2 | 0.4 | 0 |
| 3.0 | Avg (6 Samples) | 40.1 | 58.5 | 0.3 | 0.5 |
|   | Std. Dev. | 13.9 | 13.6 | 0.5 | 0.8 |
| 6.0 | Avg (6 Samples) | 44.7 | 54.5 | 0.2 | 0.3 |
|   | Std. Dev. | 12.7 | 12.2 | 0.4 | 0.5 |

Figure 6:
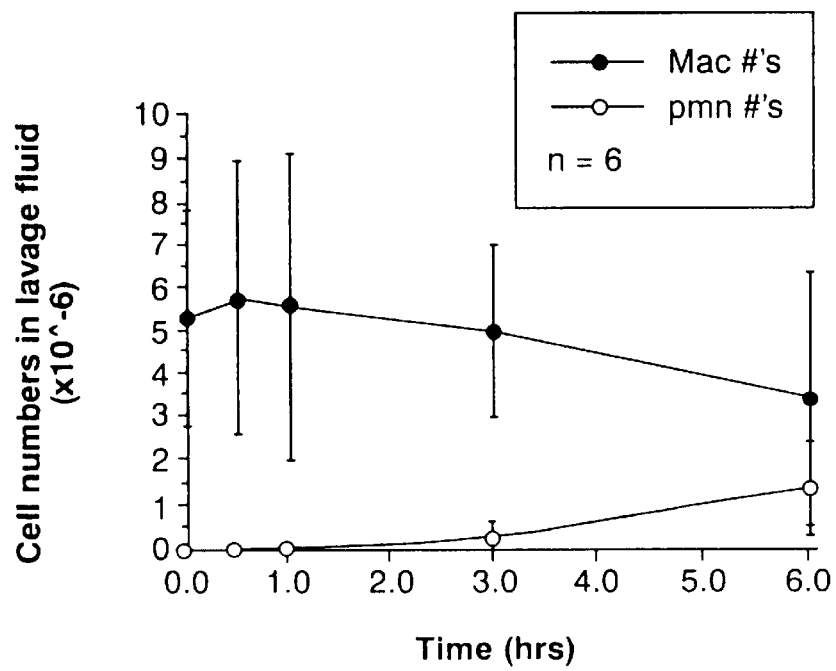

Lavage fluid: These data are presented in Table 5 and FIG. 6. A slight increase in pmns in the lavage fluid is noted about 3 hours after instillation.

TABLE 5

LAVAGE FLUID

| Hrs | | Coulter | Hemo-cytomer | Macs % | PMNs % |
|---|---|---|---|---|---|
| 0 | Avg (6 Samples) | 5.2 | 8.6 | 99.8 | 0.2 |
|   | Std. Dev. | 2.6 | 1.6 | 0.4 | 0.4 |
| 0.5 | Avg (6 Samples) | 5.8 | 9.9 | 99.8 | 0.2 |
|   | Std. Dev. | 3.2 | 4.1 | 0.4 | 0.4 |
| 1.0 | Avg (6 Samples) | 5.6 | 9.2 | 99.3 | 0.5 |
|   | Std. Dev. | 3.6 | 1.8 | 0.8 | 0.6 |
| 3.0 | Avg (6 Samples) | 5.3 | 9.0 | 92.8 | 7.2 |
|   | Std. Dev. | 1.9 | 2.2 | 9.4 | 9.4 |
| 6.0 | Avg (6 Samples) | 5.1 | 10.7 | 67.7 | 32.3 |
|   | Std. Dev. | 3.0 | 3.1 | 17.0 | 17.0 |

2. 5-Day Study

The same materials and methods as used in the 6-hour study were used, and the same parameters were analyzed.

Results:

WBC: These data are presented in Table 3 (above), as a continuation of the 6 hour study. The data are plotted in FIG. 7 which illustrates the overall circulating WBC response to pegylated G-CSF over a 5 day period. There was a rapid rise during the first 24 hours, then a decrease after 36 hours. The values return to base line after 7 days (not shown).

Figure 8:
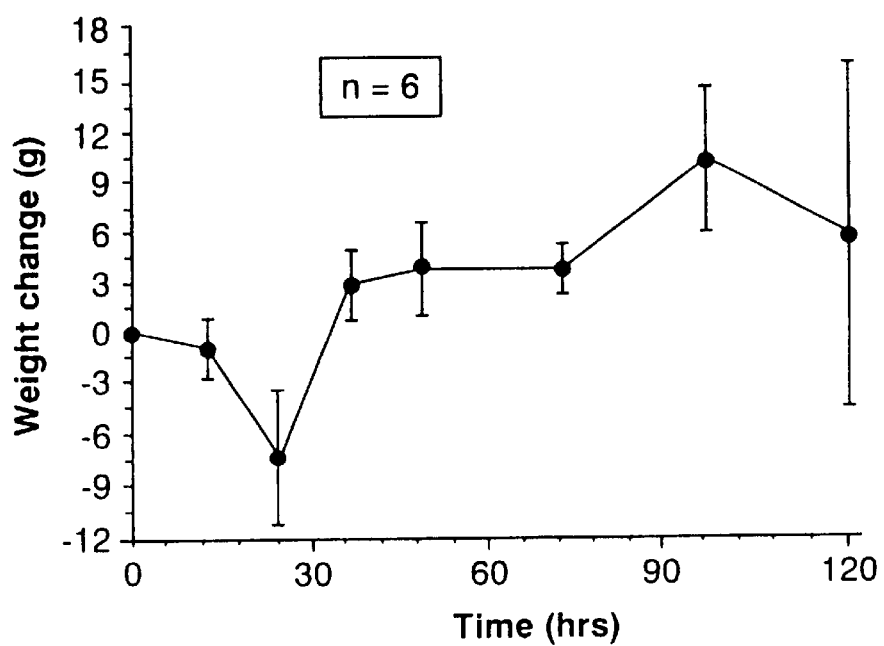
Figure 9:
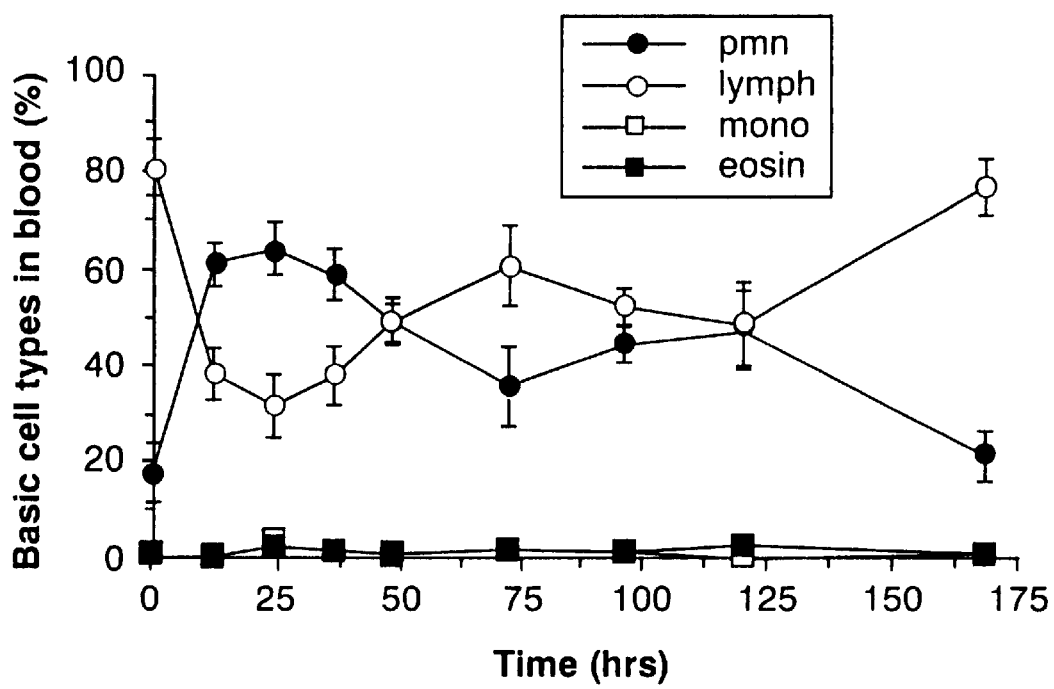

Weight Change: These data are presented in Table 6 and plotted in FIG. 8. The weight change in the animals over the 5 day period was also recorded. As found for non-pegylated G-CSF previously, some loss in weight is noted after the first day which is then recovered with a steady weight gain over the remaining time of the study.

TABLE 6

ANIMAL WEIGHT AND DIFFERENTIAL CELL TYPES AFTER ADMINISTRATION OF PEGYLATED G-CSF

| TIME (h) | 0 | 12 | 24 | 36 | 48 | 72 | 96 | 120 | 168 |
|---|---|---|---|---|---|---|---|---|---|
|  | Cntrl | | | | | | | | |
| DOSE | 105.3 | 83.2 | 87.0 | 84.2 | 92.3 | 86.7 | 87.6 | 84.2 | |
| WEIGHT | 11.3 | −1.5 | −7.3 | 2.3 | 4.0 | 4.0 | 10.5 | 6.1 | 9.3 |
| DIFF (g) | 1.4 | 1.3 | 4.0 | 2.1 | 2.8 | 1.6 | 4.4 | 10.3 | 1.3 |
| WBC | 9.2 | 19.3 | 28.3 | 31.2 | 23.2 | 12.8 | 15.8 | 13.3 | 7.9 |
| ($\times 10^3/\mu l$) | 1.6 | 4.5 | 5.0 | 10.5 | 8.7 | 3.4 | 3.9 | 3.0 | 2.8 |
| RBC | 8.4 | 9.9 | 7.9 | 9.7 | 8.7 | 9.6 | 9.4 | 9.0 | 9.2 |
| ($\times 10^6/\mu l$) | 1.4 | 1.7 | 0.7 | 0.8 | 0.8 | 1.4 | 1.0 | 1.3 | 1.1 |
| PMN (%) | 17.5 | 60.8 | 64.2 | 58.7 | 48.8 | 36.2 | 44.8 | 47.8 | 21.5 |
|  | 6.2 | 4.4 | 5.3 | 5.1 | 4.1 | 8.3 | 3.6 | 8.0 | 5.4 |
| Lymph (%) | 80.7 | 38.5 | 32.0 | 38.2 | 49.5 | 60.8 | 52.3 | 49.2 | 76.8 |
|  | 5.7 | 5.3 | 6.6 | 6.0 | 4.4 | 8.4 | 3.8 | 8.6 | 5.5 |
| Mono (%) | 0.7 | 0.0 | 2.5 | 1.5 | 0.7 | 1.7 | 1.3 | 0.7 | 0.7 |
|  | 0.5 | 0.0 | 0.6 | 1.2 | 0.5 | 1.2 | 1.0 | 0.8 | 0.8 |

TABLE 6-continued

ANIMAL WEIGHT AND DIFFERENTIAL CELL
TYPES AFTER ADMINISTRATION OF PEGYLATED G-CSF

| TIME (h) | 0 | 12 | 24 | 36 | 48 | 72 | 96 | 120 | 168 |
|---|---|---|---|---|---|---|---|---|---|
| EOS (%) | 1.2 | 0.8 | 1.3 | 1.7 | 1.0 | 1.3 | 1.5 | 2.3 | 1.0 |
|  | 0.8 | 1.0 | 1.2 | 1.5 | 0.6 | 1.0 | 0.6 | 1.8 | 1.1 |
| PMN | 1.6 | 12.6 | 18.1 | 18.7 | 11.4 | 4.8 | 7.0 | 6.4 | 1.7 |
| ($\times 10^6$) | 0.7 | 3.2 | 3.3 | 7.5 | 4.5 | 2.0 | 1.8 | 1.7 | 0.6 |
| WBC($\times 10^6$)* | 8.0 | 7.8 | 10.9 | 9.6 | N/A | 11.5 | 8.7 | 10.7 | 9.8 |
|  | 1.4 | 2.3 | 1.7 | 1.8 | N/A | 2.9 | 1.4 | 2.5 | 3.2 |
| WBC($\times 10^6$)‡ | 9.8 | 11.9 | 12.5 | 11.1 | 13.5 | N/A | 12.5 | 10.9 | 10.5 |
|  | 1.7 | 3.5 | 3.0 | 2.1 | 4.3 | N/A | 1.0 | 1.8 | 1.2 |
| MAC-BAL | 99.0 | 89.2 | 80.7 | 84.5 | 79.7 | 87.0 | 88.7 | 96.2 | 97.3 |
| (%) | 1.1 | 9.7 | 18.3 | 8.6 | 6.0 | 5.4 | 2.7 | 2.5 | 1.8 |
| PMN-BAL | 0.7 | 10.6 | 19.3 | 14.3 | 18.5 | 11.5 | 8.8 | 2.3 | 1.0 |
| (%) | 0.5 | 9.8 | 18.3 | 7.7 | 5.0 | 4.0 | 2.3 | 1.4 | 1.7 |
| OTHER-BAL | 0.3 | 0.2 | 0.0 | 1.2 | 1.8 | 1.5 | 2.5 | 1.5 | 1.7 |
| (%) | 0.8 | 0.5 | 0.0 | 1.0 | 1.6 | 1.6 | 2.7 | 1.4 | 1.6 |
| MAC-BAL | 7.9 | 6.8 | 8.7 | 8.1 | 10.7 | 10.0 | 7.8 | 10.2 | 9.5 |
| ($\times 10^6$) | 1.3 | 1.2 | 1.7 | 2.0 | 3.6 | 2.5 | 1.4 | 2.1 | 3.1 |
| PMN-BAL | 0.1 | 0.9 | 2.3 | 1.4 | 2.5 | 1.3 | 0.8 | 0.3 | 0.1 |
| ($\times 10^6$) | 0.1 | 0.9 | 2.5 | 0.8 | 1.1 | 0.6 | 0.1 | 0.2 | 0.1 |

Six animals were used for each time period. "N/A" indicates data which are not available. For the cell counts and percentages, the top number is the average, the bottom number is the standard deviation. "*" indicates a Coulter Counter was used. "‡" indicates a hemocytometer was used.

Differential Cell Types: These data are presented in Table 6 (above), and plotted in FIG. 8. There is a rapid rise in the percentage of circulating neutrophils up to 24 hours, then a steady decline over the remaining period of the study. This correlates with the WBC count, above (Table 3).

Figure 10:
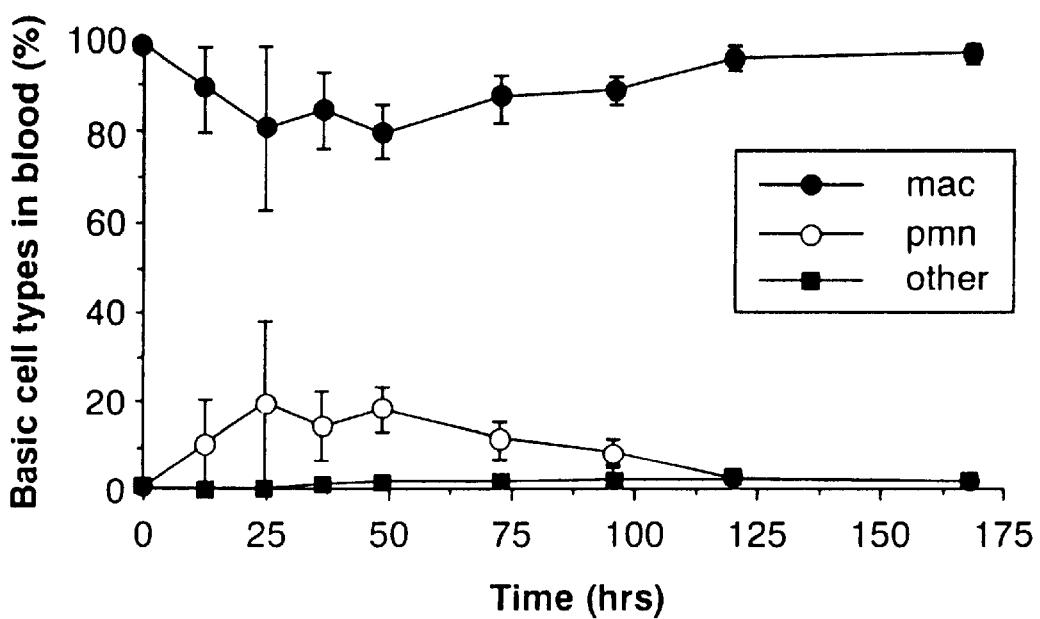

Lavage: These data are presented in Table 6 (above), and plotted in FIG. 10. As can be seen, peak percentage of neutrophils in the lung occurs at 24 hours, and returns to baseline at approximately 120 hours after administration.

3. Controls: Water, 1 mM HCl, Anesthetic, and Non-Pegylated G-CSF in Water

Control experiments were performed according to the materials and methods described above.

Five hamsters were used for each control study for dosing by intratracheal instillation. All hamsters were anesthetized by using inhaled Metafane followed by intraperitoneal injection of Brevital® (except one control group was not given the inhaled anesthetic). All solutions were filtered through a 0.22 μm Acrodisk prior to administration. Animals were sacrificed after 24 hours. Blood and BAL samples were removed for analysis of cell types and total counts as described above.

For the G-CSF in water control, dried G-CSF was dissolved in water and then instilled at a dose equivalent to 500 μg/kg.

For the inhaled anesthetic control group, a dosage of 50 μg non-pegylated G-CSF was given.

Results

Figure 11:
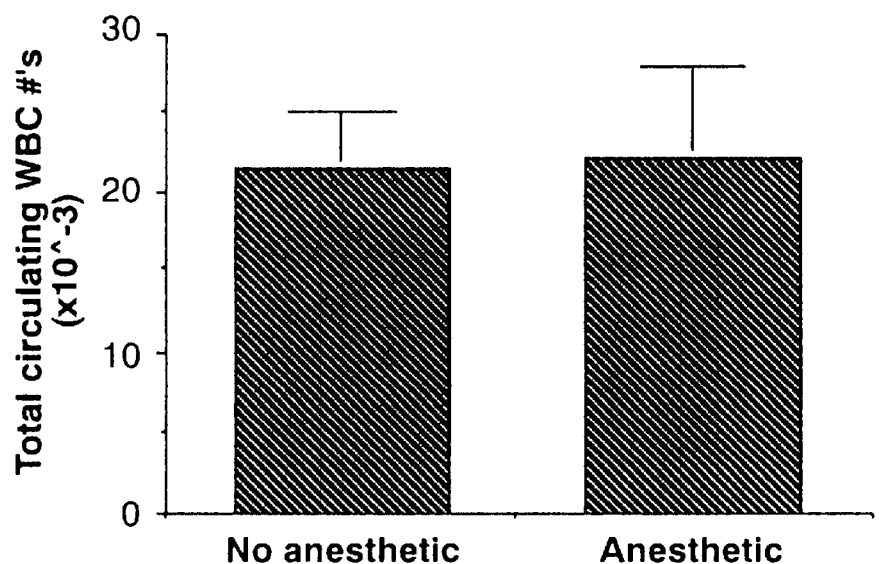

No inhaled anesthetic: These data are shown in Table 7 and the white blood cell counts are graphed in FIG. 11. As can be seen, a substantial increase in WBC count is found. There is no significant difference in the 24 hour response whether inhaled anesthetic is used or not. This indicates that inhaled anesthetic has no apparent effect on the response to G-CSF after intratracheal administration.

TABLE 7

ANESTHETIC CONTROLS

|  | 24 hr. After No Anesthetic | | 24 hr. After Inhaled Anesthetic | |
|---|---|---|---|---|
|  | Avg 5 Animals | Std. Deviation | Avg 6 Animals | Std. Deviation |
| Dose (μl) | 91.0 | 8.9 | 76.7 | 6.9 |
| Dose (μg) | 45.5 | 4.5 | 38.4 | 3.4 |
| Weight diff. | −0.5 | 1.0 | −1.3 | 1.5 |
| WBC Cnt ($\times 10^3$) | 21.3 | 3.6 | 22.0 | 5.9 |
| RBC Cnt ($\times 10^3$) | 7.6 | 0.2 | 8.3 | 1.2 |
| PMN % | 60.2 | 7.3 | 62.7 | 6.6 |
| Lymph % | 39.2 | 7.1 | 36.5 | 6.4 |
| Mono % | 0.4 | 0.6 | 0.5 | 0.6 |
| EOS % | 0.2 | 0.5 | 0.3 | 0.5 |
| BAL-Coulter ($\times 10^6$) | 7.7 | 2.4 | 7.6 | 1.3 |
| BAL-Hemo ($\times 10^6$) | 9.6 | 1.7 | 22.5 | 0.9 |
| BAL-PMN % | 17.6 | 6.3 | 25.0 | 9.4 |
| BAL-MAC % | 82.0 | 6.0 | 74.8 | 9.5 |
| BAL-OTHER % | 0.0 | 0.0 | 0.2 | 0.4 |
| BAL-MAC ($\times 10^6$) | NOT DONE |  | 5.6 | 1.0 |
| BAL-PMN ($\times 10^6$) | NOT DONE |  | 1.9 | 0.9 |

Figure 12:
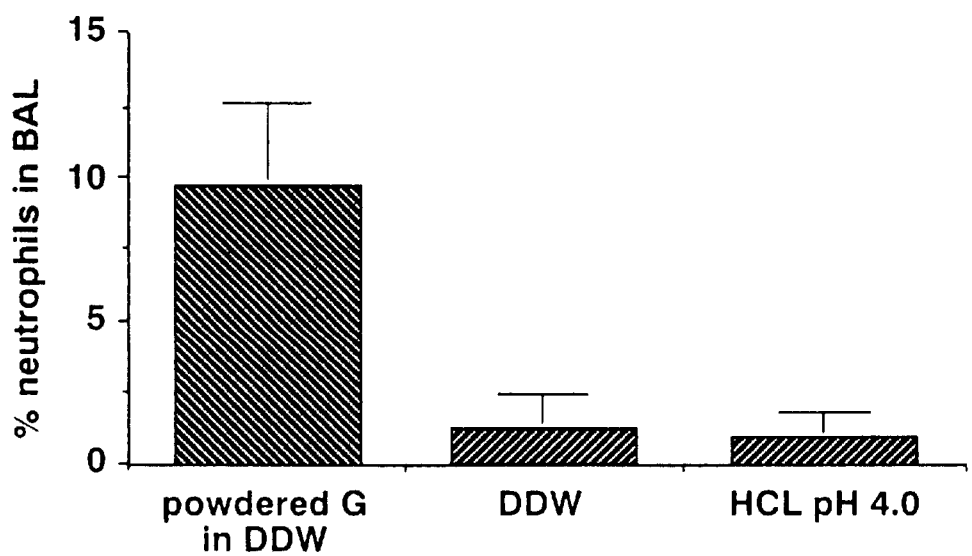

Effects of HCl or water vehicle: The neutrophil levels in the lung after administration of 50 μg G-CSF vs. HCl vehicle vs. water is illustrated in FIG. 12. As can be seen, the influx of neutrophils into the lung is by far the greatest in the presence of administered G-CSF. There is no significant difference between the neutrophil levels present in the lung after administration of water or pH 4.0 acid vehicle, indicating that the acid vehicle does not contribute to lung permeability.

EXAMPLE 6

Pharmacokinetics as Ascertained Via Immunoassay

In this study, the pharmacokinetics of pegylated G-CSF were studied in two respects: (1) the transfer of pegylated G-CSF from the lung to the circulation, and (2) the length of time pegylated G-CSF stays in the serum after instillation. Materials and methods are described above.

Figure 13:
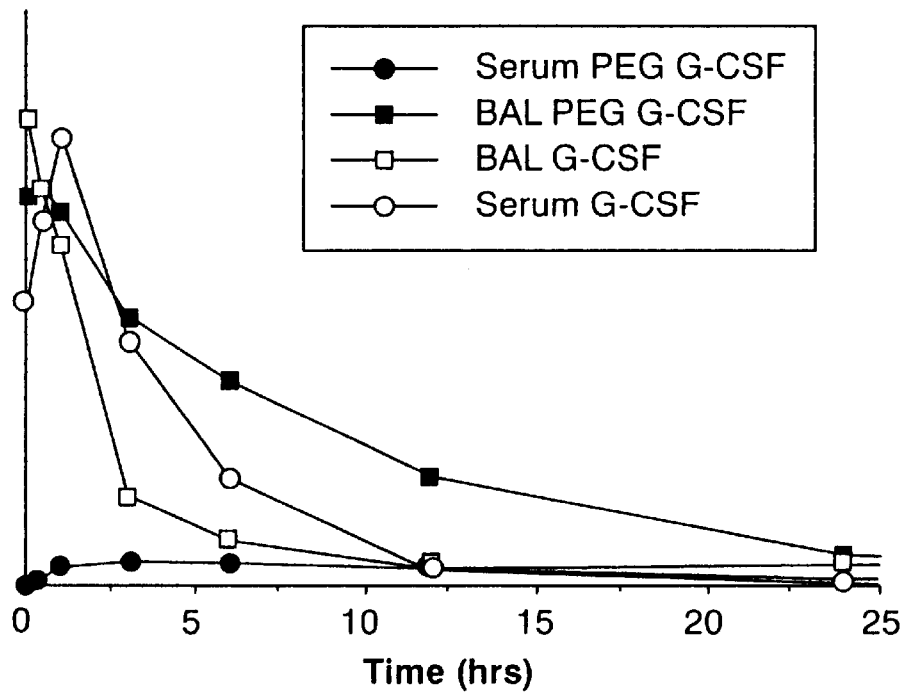

Transfer of Pegylated G-CSF From the Lung To the Serum: These data are plotted in FIG. 13 on a relative basis. The data are presented as a comparison of pegylated vs. non-pegylated G-CSF. As can be seen, the pegylated G-CSF transfers to the serum more slowly than non-pegylated G-CSF.

Serum Concentration of Pegylated G-CSF Over Time: The peak serum concentration of the pegylated G-CSF is approximately 4–5 hours after instillation, whereas the peak serum concentration for non-pegylated G-CSF is approximately one hour after instillation. Also, in this assay, the peak concentration for the pegylated material appeared approximately one order of magnitude lower than the peak concentration for the non-pegylated material, but these results may have been influenced by the sensitivity limitations of the immunoassay itself.

Figure 14:
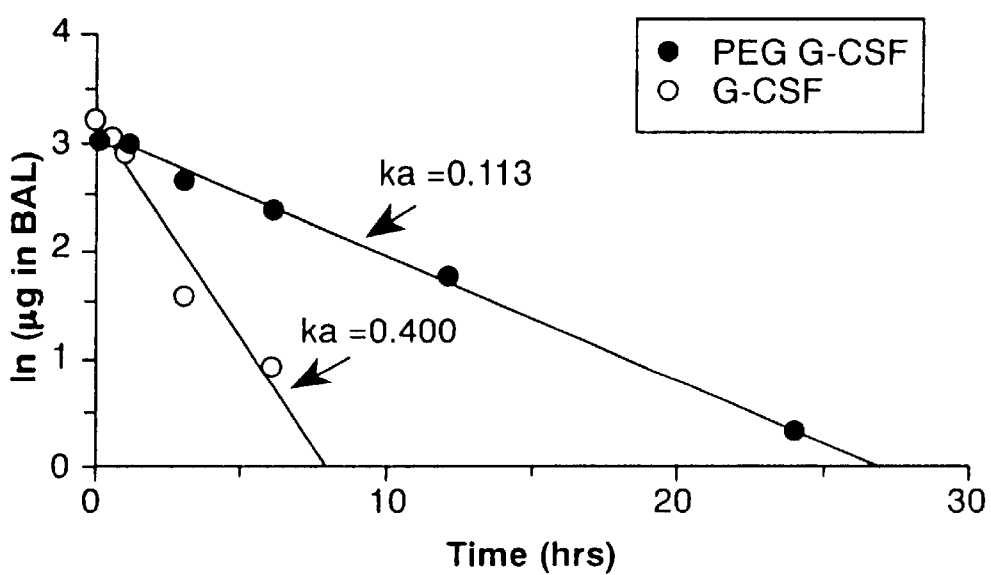

Lavage: FIG. 14 plots data for logarithmic transformation of amounts in the lung of both pegylated G-CSF and non-pegylated G-CSF with absorption rate constants. As can be seen, the pegylated G-CSF is absorbed with apparent first order kinetics.

EXAMPLE 7

Dose Ranging Study, Pulmonary Administration of Pegylated G-CSF vs SC Injection of Pegylated G-CSF In this study, routes of administration for pegylated G-CSF were compared over a range of doses. Methods used are described above.

Results

Figure 15:
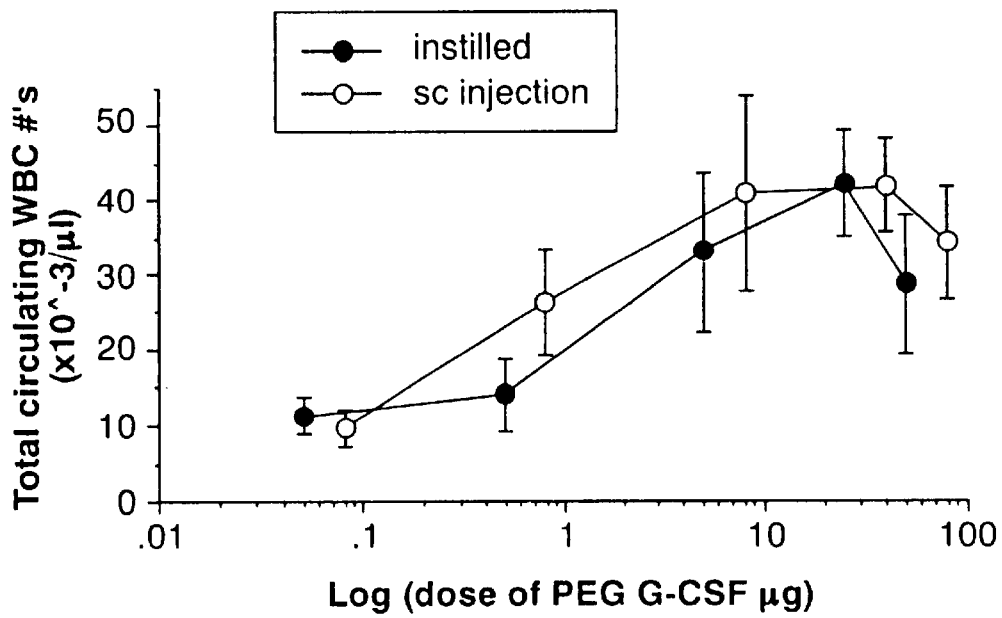

Data are presented in Table 9 (instillation data), and Table 9 (sc injection data) and FIG. 15 (plotting white blood cell count for each). As can be seen, there are similar responses in terms of total white blood cell count, and various cell differentiation.

TABLE 9

DOSE RANGING OF PEGYLATED G-CSF ADMINISTERED BY INSTILLATION, ANIMAL WEIGHT, CELL COUNTS AND CELL DIFFERENTIALS

| Treatment (100 μl) | 0.1 μg (6 animals) | 1.0 μg (6 animals) | 10.0 μg (9 animals) | 50.0 μg (6 animals) | 100.0 μg (9 animals) |
|---|---|---|---|---|---|
| Dose (wt/mg) | 97.3 4.4 1.8 | 89.2 7.7 | (ave. 3 animals = 91.6) | (not avail.) | (ave. 3 animals = 93.6) |
| Weight Diff. (24h(g)) | -0.3 3.1 1.3 | -5.8 4.8 | 2.2 3.2 | 0.7 1.2 | 1.7 1.3 |
| Total WBC (×10³/μl) | 11.2 2.4 1.0 | 14.0 4.7 | 33.3 10.8 | 42.5 7.4 | 28.9 9.5 |
| Total RBC (×10⁶/μl) | 8.6 0.6 0.2 | 9.7 0.8 | 12.3 3.9 | 14.7 2.4 | 9.7 2.1 |
| PMN % | 30.3 8.1 3.3 | 48.2 14.9 | 62.6 5.0 | 60.7 6.1 | 63.6 5.6 |
| Lymphocyte % | 66.8 10.4 4.2 | 51.7 15.1 | 36.4 4.8 | 37.3 5.8 | 34.2 5.8 |
| Monocyte % | 0.2 0.4 0.2 | 0.2 0.4 | 0.4 0.5 | 1.0 1.6 | 0.8 0.8 |

TABLE 9-continued

DOSE RANGING OF PEGYLATED G-CSF ADMINISTERED BY INSTILLATION, ANIMAL WEIGHT, CELL COUNTS AND CELL DIFFERENTIALS

| Treatment (100 μl) | 0.1 μg (6 animals) | 1.0 μg (6 animals) | 10.0 μg (9 animals) | 50.0 μg (6 animals) | 100.0 μg (9 animals) |
|---|---|---|---|---|---|
| Eosinophil % | 2.7 3.4 1.4 | 0.0 0.0 | 0.6 0.7 | 1.0 0.9 | 1.4 1.3 |
| Counts PMNs | 3.3 0.9 9.4 | 7.3 4.7 | 20.4 5.5 | 25.6 4.2 | 18.6 6.9 |

The top number in each row is the average, the next number is the standard deviation. For the 0.1 μg treatment, the third number is the standard error of the mean ("SEM").

TABLE 10

DOSE RANGING STUDY OF PEGYLATED G-CSF ADMINISTERED BY SUBCUTANEOUS INJECTION: ANIMAL WEIGHT, CELL COUNTS, AND CELL DIFFERENTIALS

| Treatment (100 μl) | 0.1 μg (6 animals) | 1.0 μg (6 animals) | 10.0 μg (9 animals) | 50.0 μg (6 animals) | 100.0 μg (9 animals) |
|---|---|---|---|---|---|
| Dose (wt/mg) | 93.5 4.2 1.7 | 91.0 3.2 | (avg. of 3 animals = 100.0) | (not avail.) | (avg. of 3 animals = 94.7) |
| Weight Diff. (24 h (g)) | 3.8 1.3 0.5 | -0.5 7.4 | 2.8 2.8 | 1.0 1.7 | 1.4 0.6 |
| Total WBC (×10³/μl) | 9.7 2.3 0.9 | 26.4 7.1 | 41.2 13.3 | 42.2 6.0 | 34.6 7.6 |
| Total RBC (×10⁶/μl) | 8.2 0.7 0.3 | 9.8 0.7 | 13.5 4.5 | 14.0 1.6 | 10.0 3.5 |
| PMN % | 26.3 5.1 2.1 | 59.0 0.3 | 58.6 4.2 | 59.3 5.6 | 66.3 4.8 |
| Lymphocyte % | 72.7 4.3 1.7 | 39.7 5.5 | 40.3 4.3 | 39.5 6.2 | 31.8 3.7 |
| Monocyte % | 0.0 0.0 0.0 | 0.0 0.0 | 0.6 0.9 | 0.0 0.0 | 0.8 0.4 |
| Eosinophil % | 1.0 1.6 0.6 | 0.7 0.8 | 0.6 0.7 | 0.5 0.8 | 1.1 1.3 |
| Counts PMNs | 2.6 0.9 0.4 | 15.7 5.3 | 24.3 8.5 | 25.0 4.0 | 22.9 5.3 |

The top number in each row is the average, the next number is the standard deviation. For the 0.1 μg treatment, the third (bottom) number in each row is the SEM.

Figure 16:
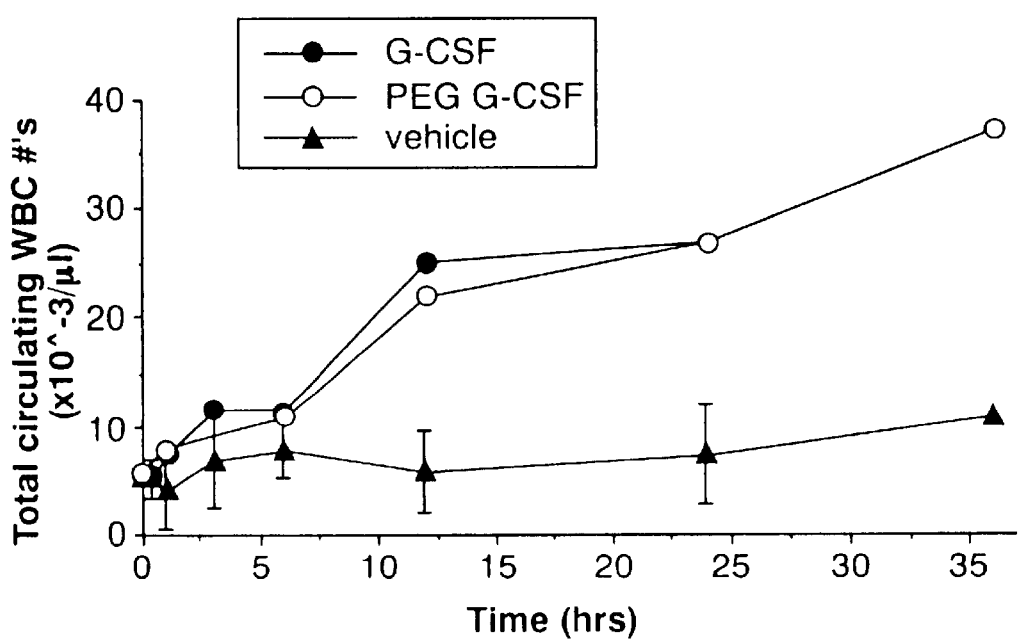

WBC: Particularly, as shown in FIG. 16, the white blood cell count steadily increased for both forms of administration of pegylated G-CSF. There is a time lag in response at the low dose levels for pegylated G-CSF, because of the time ($t_{1/2} \approx 6.1$ hours) for sufficient pegylated G-CSF to penetrate the pulmonary barrier and initiate a response. This lag is not apparent at higher doses, however, and one can see that even the low fractional transfer of pegylated G-CSF to the circulation within approximately one hour at doses used is sufficient to elicit a maximal response.

EXAMPLE 8

Elimination Kinetics of Intra-Cardiac Injection of Pegylated vs. Non-Pegylated G-CSF This study relates to the elimination kinetics and effects of intra-cardiac injection of pegylated G-CSF vs. non-pegylated G-CSF. Comparisons were made of such intra-cardiac injection to pulmonary administration. For this intra-cardiac administration study, a dose of 500 µg/kg was given to each animal, and 5 animals were sampled for each pegylated G-CSF/non-pegylated G-CSF, at time points of 0.1, 0.5, 1, 3, 6, 12, 24 and 36 hours. For the acid vehicle (pH 4.0) control, 3 animals were used at each time point, except for 0.5 hours, where 2 animals were used. Materials and methods are as described above.

Results

Results are presented in Table 11 and FIGS. 16, 17, and 18.

TABLE 11

COMPARISON OF PEGYLATED G-CSF WITH NON-PEGYLATED G-CSF: WHITE BLOOD CELL COUNTS AFTER INTRACARDIAC ADMINISTRATION

| Time (hrs) | # | G-CSF WBC #s | PEG G-CSF WBC #s | Vehicle WBC #s |
|---|---|---|---|---|
| 0.1 | avg | 5.5 | 6.1 | 5.5 |
|  | stdv | 1.6 | 1.2 | 0.3 |
| 0.5 | avg | 5.5 | na | 5.4 |
|  | stdv | 1.7 | na | 1.7 |
| 1 | avg | 7.9 | 8.2 | 4.4 |
|  | stdv | 3.6 | 1.5 | 3.7 |
| 3 | avg | 11.8 | na | 7.2 |
|  | stdv | 1.5 | na | 4.3 |
| 6 | avg | 11.6 | 11.2 | 8.1 |
|  | stdv | 4.0 | 4.9 | 2.6 |
| 12 | avg | 25.0 | 22.0 | 6.1 |
|  | stdv | 5.9 | 6.2 | 3.8 |
| 24 | avg | 27.1 | 27.2 | 8.1 |
|  | stdv | 12.1 | 6.7 | 4.6 |
| 36 | avg | na | 37.4 | 11.6 |
|  | stdv | na | 14.9 | 0.2 |

WBC count: Table 11 shows data for white blood cell counts for (i) non-pegylated G-CSF, (ii) pegylated G-CSF, and (iii) acid vehicle alone (HCl, pH 4.0). These data are plotted in FIG. 16. As can be seen, there is an increase in white blood cell count after a single intra-cardiac injection of 500 µg/kg G-CSF, whether pegylated or non-pegylated, and this increase is not seen with the control.

Pulmonary administration vs. Intra-Cardiac Administration: A comparison was made between previous data obtained for the WBC response after intra-tracheal instillation and the intra-cardiac injection of pegylated G-CSF. These data are plotted in FIG. 17.

As can be seen, surprisingly, the white blood cell profiles appear to be similar for both routes of administration, whether through the lung or directly to the blood via the heart. This is surprising because a time lag would have been expected. As demonstrated by immunoassay data above, roughly half of the instilled dose is available for absorption from the lung to the blood stream. The present study indicates that even a small fraction of the pegylated G-CSF presented to the circulation within 1 to 2 hours post-dosing would be sufficient to exert a profound effect on WBC numbers.

When non-pegylated G-CSF is compared (pulmonary administration vs. intra-cardiac injection), there are apparent differences in response time. FIG. 18.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A method for the systemic administration of pegylated granulocyte-colony stimulating factor (G-CSF), comprising depositing a therapeutically effective amount of said pegylated G-CSF optionally in a pharmaceutically acceptable carrier in the lungs of a mammal in need thereof while the mammal is inhaling.

2. A method according to claim 1 wherein said pegylated G-CSF is in the form of a solution in an aqueous medium or a suspension in a non-aqueous medium.

3. A method according to claim 2 wherein said pegylated G-CSF optionally in a pharmaceutically acceptable carrier is in the form of a powder.

4. A method according to claim 1 wherein said G-CSF is pegylated with at least one polyethylene glycol molecule having a molecular weight of between about 500 and 20,000 Daltons.

5. A method according to claim 4 wherein said molecular weight is at least about 600 Daltons.

6. A method according to claim 4 wherein said molecular weight is about 6000 Daltons.

7. A method according to claim 1 wherein said G-CSF is pegylated with at least one polyethylene glycol molecule, said polyethylene glycol molecule being in solid form.

8. A method according to claim 1 wherein said G-CSF is pegylated with more than one molecule of polyethylene glycol.

9. A method according to claim 8 wherein said G-CSF is pegylated with 2 to 5 polyethylene glycol molecules.

10. A method according to claim 1 wherein said pegylated G-CSF is delivered to the lungs of said mammal from a mechanical device suitable for pulmonary administration and capable of depositing said pegylated protein in the lungs of a mammal.

11. A method according to claim 10, wherein said mechanical device is a nebulizer, metered dose inhaler or powder inhaler.

12. A method according to claim 11 wherein said mechanical device is a nebulizer.

13. A method according to claim 12 wherein said nebulizer is ultrasonic.

* * * * *